United States Patent [19]

Macias et al.

[11] Patent Number: 4,851,816

[45] Date of Patent: Jul. 25, 1989

[54] CRIB DEATH (SIDS) WARNING DEVICE

[76] Inventors: Helene Macias; Angos Winke, both of 5333 Russell Ave., Ste. 301, Hollywood, Calif. 90027-3513

[21] Appl. No.: 18,335

[22] Filed: Feb. 24, 1987

[51] Int. Cl.[4] ............................................. G08B 23/00
[52] U.S. Cl. .................................... 340/573; 128/886
[58] Field of Search .............................. 340/573, 604; 128/138 A, 886; 200/61.04–61.05

[56] References Cited

U.S. PATENT DOCUMENTS

| | | | |
|---|---|---|---|
| 2,127,538 | 8/1938 | Seiger | 128/886 |
| 2,687,721 | 8/1954 | Ellison | 128/886 |
| 2,812,757 | 11/1957 | Lusk et al. | 128/886 |
| 3,025,858 | 3/1962 | Browner | 128/422 |
| 3,245,068 | 4/1966 | Wegryn et al. | 340/573 |
| 3,441,019 | 4/1969 | Snyder | 128/886 |
| 3,460,123 | 8/1969 | Bass | 340/573 |
| 3,480,010 | 11/1969 | Crossley | 128/132 R |
| 3,508,235 | 4/1970 | Baisden | 340/573 |
| 3,530,855 | 9/1970 | Balding | 128/886 |
| 3,696,357 | 10/1972 | Kilgore | 340/573 |
| 3,778,570 | 12/1973 | Shuman | 340/604 X |
| 3,818,468 | 6/1974 | Toth et al. | 340/573 |
| 3,971,371 | 7/1976 | Bloom | 128/886 |
| 4,106,001 | 8/1978 | Mahoney | 340/604 |
| 4,163,449 | 8/1979 | Regal | 340/573 X |
| 4,191,950 | 3/1980 | Levin et al. | 340/604 |
| 4,212,295 | 7/1980 | Snyder | 128/886 |
| 4,279,257 | 7/1981 | Hochstein | 340/573 X |
| 4,356,818 | 11/1982 | Macias et al. | 128/138 A |
| 4,438,771 | 3/1984 | Friesen et al. | 340/573 X |
| 4,484,573 | 11/1984 | Yoo | 128/886 |
| 4,539,559 | 9/1985 | Kelly et al. | 340/573 |
| 4,653,491 | 3/1987 | Okada et al. | 340/573 X |
| 4,688,027 | 8/1987 | Widener | 340/573 X |

FOREIGN PATENT DOCUMENTS 1174346 5/1968 United Kingdom .

Primary Examiner—Glen R. Swann, III
Assistant Examiner—Thomas J. Mullen, Jr.

[57] ABSTRACT

An apparatus for specific fluid detection in prophylactic prognosis of a medical condition known as Sudden Infant Death Syndrome, that in one embodiment features a casing which is removably affixable to a sensor configured for receiving and transmitting the information of manifestation of micturition to an embodied acquisitioning accommodation embracing a variable frequency oscillator, the output of which interconnects with a signal converter conceptualized to transition a switching provision into energizing a built-in alarm system consequential to the signal converter's having sampled and found the oscillator's frequency to be representative of a manifestation of micturition in precursor to a CNS agonal episode derived laryngospasm attack, while in another embodiment, a switching structure provides for the energizing of an alarm configuration that injects its modulation into the signal circuitry of a baby listening device, and in yet another embodiment, provides for the switching on of a code modulator and thereto connected propagation device in a manner for propagating the information of manifestation of micturition to an independent capture accommodation connected to a compatible signal converter that is conceptualized upon such code's acquisition to consequently cause the transition of a switching faculty, the configuration of which, results in a bi-directionally spliced signal flow of which one is directed to initiate the tasking of a multi-ported microprocessor that controls an ACLS arrangement operationally architectured to induce increased negative intrathoracic pressure relief when not cancelled by supervising personnel or the microprocessor itself accessing the receipt of data that is comprised of co-processed signals.

41 Claims, 4 Drawing Sheets

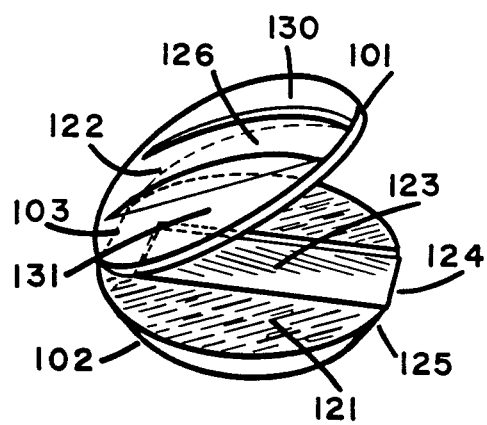
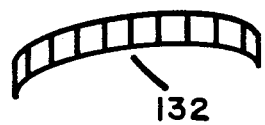
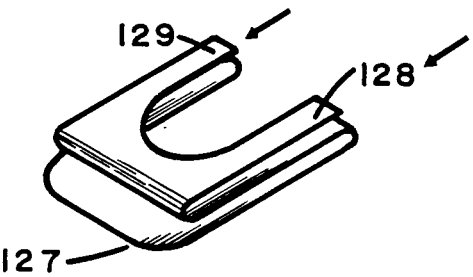
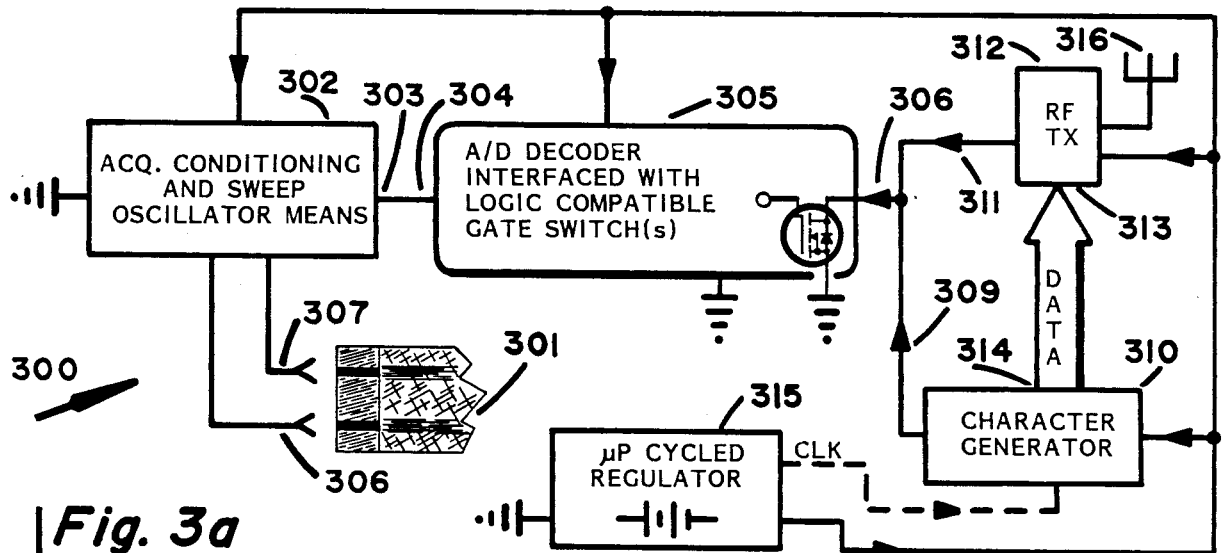
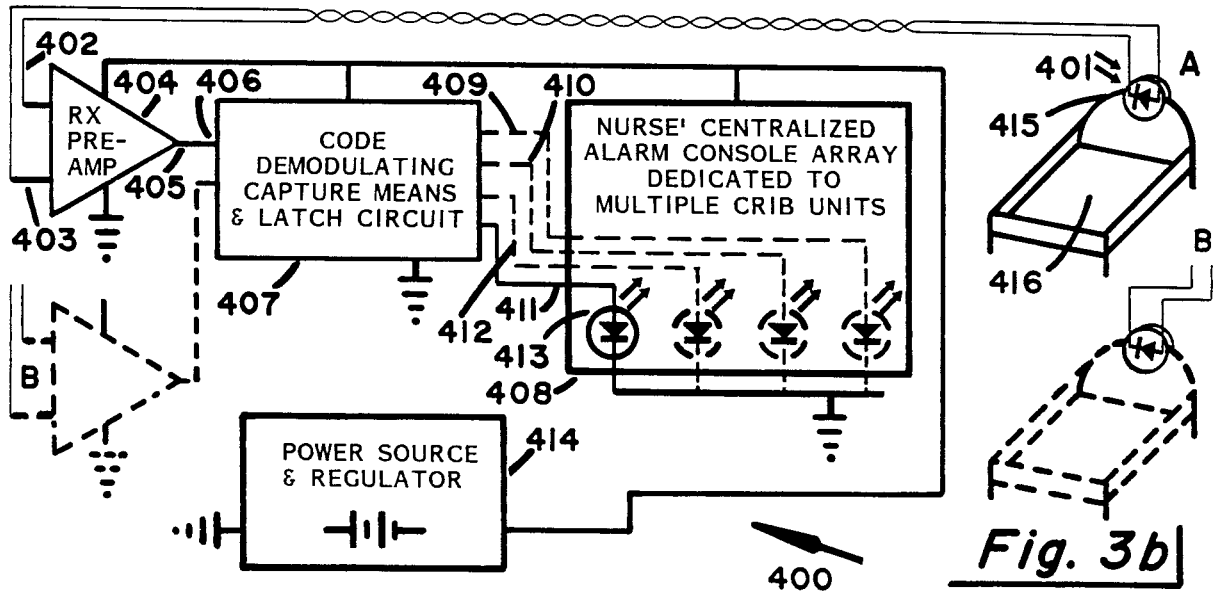

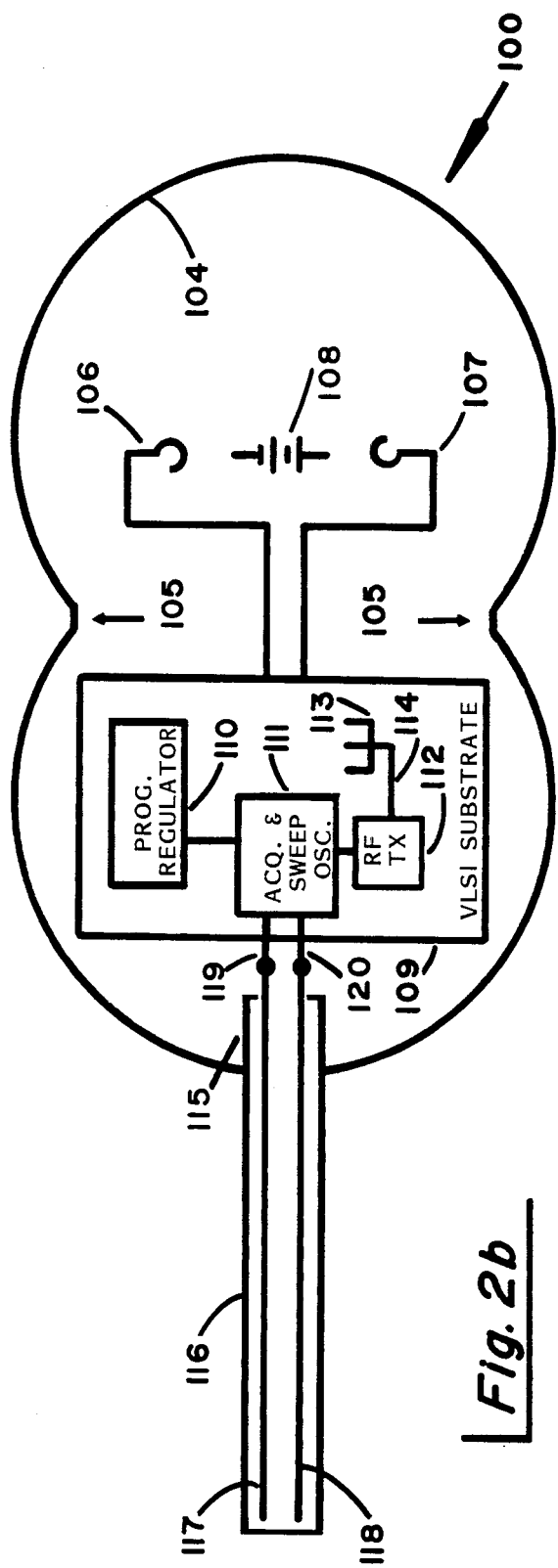
Fig. 2b
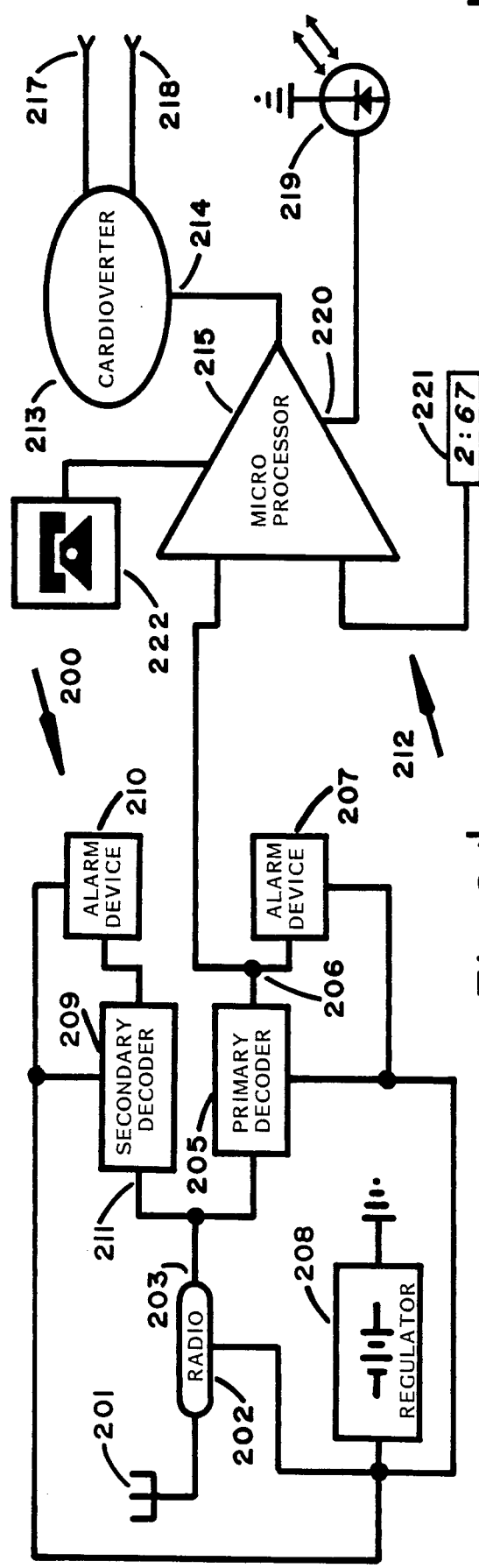
Fig. 2f
Fig. 2d

CRIB DEATH (SIDS) WARNING DEVICE

BACKGROUND OF THE INVENTION

This invention relates to a system for detecting the moment of micturition in babies.

More particularly, this invention relates to a system which will interdict enuresis alarm circuitry incorporated in it or attached to it from being tricked into switching itself on when in fact the sensor striping, screens, clips or stripes used in and with swaddles or latest embodiment the plastic layered disposable diaper is not wet with urine but condensation permeated.

An inspection of the numerous art precursive to this invention amply demonstrates that enuresis monitors continue to present a challenge to practitioners in the art.

Although in the past, discoveries have resulted from a need to cater to the more obvious and embarrassed group that comprises higher age groups, our investigations have uncovered a critical area not previously challenged by others. Namely that a properly conceived micturition detector, when conceptualized standing alone or configured as an integrally featured structure of a disposable diaper, could possess the ability to alert a mother or other person to prognose agonal motor activity that is commonly associated with 85% of "Sudden Infant Death Syndrome" related deaths.

Because a CNS agonal episode of motor activity triggers a voiding of a baby's bladder, a prompt reaction with proper management of known resuscitation techniques will invariably result in a reduction of deaths caused by asphyxia or increased intrathoracic pressure resulting from involuntary neonatal laryngospasm, a condition that in babies has been diagnosed to be not unrelated to the common spasmodic "hiccough" generally well tolerated in higher age groups.

Whereas the authoritative Merck Manual, fourteenth edition, published by Merck Sharp & Dohme Research Laboratories, indicates that annually some 10,000 infant deaths reflect a "SIDS" (i.e., crib death) related classification, any help that breaks new ground in the art and can contribute to promoting fewer deaths, will obviously be beneficial to the public. By analogy, whereas 1 in every 350 live births in the United States of America terminates as a fatality to "SIDS," that statistic constitutes an unacceptable ratio by any measure, and it is to the improvement of that statistic that the novelty of this invention is addressed.

Although it is acknowledged that most voidings are generally not agonal episode related, a cautious attitude is nevertheless properly indicated, in particular, where for some medical reason or other reason, the parent(s) is precluded from conceiving a further offspring.

In the past, numerous systems have been conceived which purported to be micturition event monitors, but most suffered to one degree or other from an unacceptable susceptibility to switching "ON" in response to mediums other than urine.

Notwithstanding in diversity remarkable and without doubt creative, the teachings of the prior art, taken broadly, have either not become commercially reproducible or have not seen their commercial production because of a failure to perform in real life as true micturition event monitors.

While it is true that the majority of the prior art has characterized itself as micturition event monitors, the assumed characterization has been found to possess little more than a grain of truth owing to the prior art having unfortunately misplaced its reliance on an erroneous proposition concerning the means to economically capture, identify and staff off the associated electronics from switching itself "ON" when micturition had not taken place.

Putting the case to point, the prior conceptions have failed to recognize the novelty that the effluent of urine offers a specific and measurable advantage over equally present and sharing mediums that generalized comprise perspiration condensation, related crotch surface lubricants, and higher up, involuntary nocturnal saliva escapes, and accordingly, urine's identification not being an easily palpable medium by heretofore arrangements or constituents of cloth or wire, no matter how ingeniously crafted. To their credit, some are indeed creditably more confortable than others in modern day applications where disposable diapers constitute the normal attire of babies whether berthed in the crib or on the go with today's traveling moms, but that is not the primary issue that we are speaking to.

It is in this misconceived concept that each prior patentee(s) alleges his or her invention an improvement over the referenced antecedent art, and has accordingly offered forth ever more unwieldly or commercially difficult to duplicate constructions for their "sensing" extensions or related peripherals to try and help overcome the propensity of associate alarm circuitries from being fooled into switching "ON" at the onset of perspiration condensation in the crotch area—instead of waiting and holding off switching said associated alarm circuitries "ON," until the event of actual micturition had factually manifested itself.

Quite obviously, none of the prior art has conceived the palpability of micturition manifestation by means of a sweep frequency oscillator terminating in a predesignated ratio demodulation system as indicated by the technique shown in this invention.

Whereas some early art characterized by U.S. Pat. Nos. 2,812,757; 3,696,357 and 4,163,449 downplay the tragic interference and "masking effect" that perspiration condensation problems in diapers cause systems when trying to acquisition the manifestation of micturition, by providing "sensitivity" potentiometers, as if thereby could obviate the preemptory interference caused by perspiration condensation imitating partial enuresis. Regal U.S. Pat. No. 4,163,449 in particular appears oblivious to its intrinsic limitations to a successful employment in neonatal management, by the obvious necessity that a baby would have to sleep naked and without the sanitary benefit of a diaper. This is so on account of the very nature of a baby's usually wearing of a diaper, and diapers, by reason of incorporated "elastic gathers," entrapping any effluent of urine from seepage into and soiling of the baby crib's sheeting, thereby consequently rendering any Regal or a likewise sensor bedpad device such as the Shuman U.S. Pat. No. 3,778,570, to be not only ineffective and superfluous, but to also be incompatible with ancillary baby care products as envisioned by the Friesen U.S. Pat. No. 4,438,771, entitled "Passive Contactless Monitor For Detecting Cessation of Cardiopulmonary Activity." Our invention on the other hand, can be used with any presently envisionable ancillary baby care products without concern on the part of parent or medical practitioner; and further, does provide numerous accessories for adaptation to its employment in unusual circumstances such as would be desirable with elderly users of disposable briefs because of loss of bladder control, available among others under the brand names of "Depends" or "Attends," as manufactured by the company of Procter & Gamble; and further still, will invariably hold off triggering any range of conceivable alarm circuitries, including unobtrusive pocketable tremblers, in the absence of a true micturition manifestation.

Other early art characterized by U.S. Pat. Nos. 2,127,538; 2,687,721; 3,245,068; 3,460,123; 3,971,371; 4,106,001 and 4,212,295 have skipped altogether and taught naught that might have shed light on the difficulty of suppressing premature perspiration-caused switching "ON" of the signal control apparatus, because the conceivers of the art simply had not conceptualized or could offer to the consumer a viable alternative to a knotty problem, which consequently left it up to the consumer to deal with the occurrence of false alarms in each own's fashion. Where we have been able to observe a definite limitation with the Regal patent, we are likewise disposed to identify that the Shuman patent similarly require that a baby lay naked in order for the Shuman device to function as prescribed, and it is for that reason, and the relational fact that all linen and blanketing would thereby find their repeated contamination conferred an undesirable coloration, that an objectionable appearance of uncleanliness has limited the desirability to lay babies naked on these manner of sensor bedpads, whatever may have been their means of construction, whether assembled by sandwiching absorbent pads and metal screens, or manufactured by laminating from multiple supply reels, or by stitching with metalized thread, a plurality of thin current conductive sensor strips to a predominant side of a presized thin bedpad of supportive substrate.

Taking a different approach, Baisden U.S. Pat. No. 3,508,235 sought to leverage a galvanic principal comprising dissimilar metals (i.e., zinc-silver) to generate a voltage in the presence of urine, but again failure was inevitable because, by test, fluids other than urine measured confusingly comparable EMF, using a JOHN FLUKE model 8200A D.V.M.

The majority of subsequent art characterized by U.S. Pat. Nos. 3,530,855; 3,696,357; 3,818,468 and 4,191,950, broke new ground by employing a free-running multivibrator conceived to output a fixed frequency upon the conductivity of urine simulating the closing of an electrical switch. But once again that art refused to fulfill its promise to hold off from switching "ON" except in the event of actual micturition, and finds its subsequent abandonment as preferred in U.S. Pat. No. 4,191,950, where based upon United Kingdom Pat. No. 1,174,346, Levin U.S. Pat. No. 4,191,950, interposes a variation on a Schmitt trigger between the "sensor" and a fixed frequency outputting into a speaker.

Reviewing the more recent art visible in U.S. Pat. Nos. 4,191,950; 4,484,573 and 4,539,559, and purchasing their marketed embodiments, we found the inventors denying the claimed exclusiveness of conception—by confessing in related instruction manuals, namely. "While the baby urinated or sweated much, its moisture will drive the switch of the baby bell." And indeed, multiple units procured to exclude defective samples have confirmed that all of them invariably preemptively triggered "ON" upon coming into contact with nothing more than oral saliva.

Studying the most recent proponents of the art, embodied by U.S. Pat. Nos. 4,356,818; 4,484,573; 4,539,559; 4,653,491 and 4,688,027, we find that the Okada U.S. Pat. No. 4,653,491, is a progeny of our earlier Macias U.S. Pat. No. 4,356,818, in particular with respect to our unique longitudinally extended metal layer being covered with a layer of electrical insulating material (i.e., FIGS. 3a, Nos. 130 and 131; in FIG. 3b, Nos. 13 and 26; and FIG. 13, Nos. 130 and 131. (all in the Macias patent)). Although essentially a tracing from our earlier patent, it should be noted that here again reliability is not guaranteed by the terms of the Okada patent (column 3, lines 1–7) in that had Okada included the features depicted in the Macias's patent as shown in FIGS. 8, 9, 10 and 11, Okada need not have had to warn against variations arising in the distance separating his metal layers, and thus need not have had to caution against capacitance uncertainties which arise when Okada's metal layers get crushed in the crotch of the wearer. Furthermore, Okada makes clear that his conception relates to a quantitative measurement of perspirated condensation (i.e., water) by the change it engenders in capacitance, proportional to area, rather than a qualitative measurement of urine manifestation.

As regards the Widener U.S. Pat. No. 4,688,027, we can appreciate the merits of his wipeable isolated molded sensor strip, although we cannot lose sight of the fact that in the Widener construction, placement of the strip appears to be critical in that only side of its "flats" is receptive to interrogating an adjacent surface—because only one side of the flats 12 is provided with a pair of groovings 38 and 40, filled with conductive material 14 and 16. It appears to us that the better arrangement would have been to have had the obverse "flat" (i.e., back-to-back) be similarly arranged, but we also recognize that Widener might have elected not to similarly accomodate the obverse side of the "flats" because of encountered difficulties with cracking or indeed breaking off of lengths of the strip due to fatigue of the sensor strip assembly, thereby resulting in a premature shortening of the strip and rendering useless the most expensive part of the strip, namely, the molded yoke assembly 18 comprising discrete resistors 30 and 32, and molded in place shielded cable 22 and plug 24. As will be further noted, the extreme emphasis Widener places on the use of shielded wire, by necessity infers that environmentally induced spikes or charges (i.e., by refrigerators, vacuum cleaners, etc.) will cause the proposed circuitry into unnecessarily triggering a false moist condition. Additionally, Widener has not acknowledged that there exists a 50/50 chance that the strip will not function when "For the primary application of sensing urine, sensor strip 12 is placed in the bedding within an absorbant pad between the sensor strip 12 and the patient." (column 4, lines 66–68), this because many a person will inadvertantly place the active "flat" of the strip face down, and thus pointed away from the source of urination; or the end of the strip opposite to the yoke's opening as claimed by Widener to be functional as a securing location for affixation by clip (column 3, lines 62–65), may even curl away or be involuntarily displaced to one side when the patient turns or moves in the restless tussle of sleep. Furthermore, it seems that Widener has left the erroneous impression that Shuman taught fabricating a urine-sensing pad on a roll which may be cut (supposedly by the consumer) to any desired length (column 1, lines 13–16). In fact a close reading of Shuman clearly discloses in column 1, lines 50–57, that a number of additional manufacturing steps are required before the product of the Shuman invention would have been ready for sale to the consumer, with Shuman's retail sales accordingly projected to have been on a pre-sized bedpad to bedpad basis.

From a clinical perspective, none of the prior art has been entirely successful whether the art having spawned as the result of a reduction to practice inconsistent with comfortable wearing as conceived in U.S. Pat. No. 3,441,019, or more recently as a result of efforts to narrow or lower the acceptance range in which toggelling by the signal control means genuinely causes a fixed audio frequency signal generator means to activate, immaterial whether the input to the signal control means be referenced to the high rail as shown in U.S. Pat. Nos. 3,441,019 and 4,191,950, or predisposed by trickle resistor as taught in U.S. Pat. No. 4,539,559.

From a different perspective, we have become well acquainted with cessation of respiration monitors, especially by Hewlett-Packard, because back in the 1960's, when we were conducting studies on parasitic interactions with other connected devices then typically in use in hospitals' neo-natal care suites, it is quite true, although not stated in Friesen U.S. Pat. No. 4,438,771, but referenced in Hochstein U.S. Pat. No. 4,279,257, that at that time, the most prominent of these devices, especially from the perspective of those available to the general public apart from the more specialized surgical suite instruments, that the instrument of choice was one that constituted slipping a retracting expansion belt about the chest of the patient, the umbilical cord of which was appropriately attached to a monitoring device placed on a table next to the patient's bed. Other devices not generally thought of as aspiration cessation monitors, but nevertheless could have been initially specifically so intended if had been intentionally so configured from their inception, are available in known and several variations on the theme presently known in the art as electronic snore depressors, a well known example for the study of this art and derivatives finding a good foundation in Crossley U.S. Pat. No. 3,480,010.

Although we respect the achievements made by Hochstein and Friesen, regretfully, neither the Friesen nor the Hochstein device will achieve their assumed popularity, because their employment will not prevent irreversible brain death, or severe tissue damage that will result (a) in permanent disability as a consequence of resuscitation applied too late, and, (b) as a result place the unfortunate parent(s) in a financial, emotional and spiritual struggle that is of enormous complication, this in essence because of oxygen deprivation of brain tissue cells that will have occurred before reflexive cardio-pulmonary relaxation will have permanently set in and connected alarms, designed to registering said relaxation as proposed by Friesen or Hochstein having sounded off.

A parential's close monitoring, on the other hand, of baby's micturitional displays, especially during the afternoon napping period when the majority of SIDS attacks take place (i.e., a REM related Hallucinatory neural activity not having been determined dispositive of contributory excitation) makes its own positive statement, in particular given the fact that an agonal motor activity attack will in likeness to an idiopathic (e.g., birth trauma) epileptic seizure, result in fecal and urinary incontinence. Because of the short time span between agonal motor activity onset and a micturition display, a shortened reaction time is afforded by the use of our invention over the Friesen or Hochstein devices which by their inherent teachings will have patiently continued to average out the reflexive costal regional convolutions preceeding cardio-pulmonary collapse until long after our invention will have sounded off, and in accordance with this prompt attention afforded by our invention over the Friesen or Hochstein inventions that react too late in the agonal cycle, the baby under properly caring observation need never face the prospect of being subjected to suffering from such prolonged oxygen deprivation that sadly erodes the practicability that went into the creativety underlying the Friesen or Hochstein inventions.

In recent years, high performance electrochemical detection has become commonplace, with salinity and conductivity meters available to anyone. Although the laboratory or industrial setting suits the available means, nothing is available to mothers in the scope of a device no larger than a couple of "half-a-dollar coins" stacked flat one on top of the other.

Regardless of the modes employed, be it by amperometric detection or across wheatstone bridges, heretofore available means have failed to conceptualize the novelty of "task specific toggelling," and all suffer from undue encumberances which include the need for a minimum off-set and temp-drift in the front end interface, a costly and blown proposition for the intended application; a manipulatable bias adjustment screw with its size and need for precision; an indicating device such as a meter or "magic eye" to show when the base line has been appropriately adjusted when null determining the bias potentiometer (10-turn); and last but not least in the case of electrochemical detectors, three (3) connecting leads feeding into the potentiostate out of conductivity cells generally made of glass or plastic material (configurated as gel-filled bulbs or double junction wands), or in the case of probes usual with salinity and conductivity meters, precious metal plated electrodes rigidly constrained in a strict relationship in probe housings and by their very inherent requirements, utterly unsuitable to monitor in the area of interest by baby.

SUMMARY OF THE INVENTION

By contrast to heretofore teachings, we instead, herewith have path found for others what we are informed and believe to be non-obvious, and a novel and better way to interrogate, manage and display accurately, information captured in acquisitioning the occurrence of a specific biological fluid in a particular area of interest.

It is another object of this invention to provide an interlock means connectable into the logic program of a task scaled cardioverter (ACLS) procedure to cause a baby's aspiration modelity to react hypercinesiatic until defeat of the strangle hold that accompanies the onset of the grip of increased negative intrathoracic pressure as a result of laryngospasm (crib death).

It is a further object of this invention to provide mothers with a true agonal episode triggered micturition event monitor that is comparable in quality to what we have gratefully become accustomed to with the venerable NAGRA ® self-contained tape recorder conceived by Mr. Stephan Kudelski.

It is still another object of this invention not to provide mothers with yet another of the already numerously compared water activatable alarms, but instead, to provide mothers and health care providers with a signature reactive micturition occurrence alarm, conceptualized and addressed to economically offering various levels of sophistication in execution without losing sight of maintaining actuality of occurrence assurance in furtherance of crib death crisis abatement management.

It is yet another object of this invention to provide an open architecture permissive of additions, substitutions or creative integration with for instance peak limiting, detection diode pulse integrated op amplified indicators wherever handshaking is expeditious the multifarious implementations that our invention would support.

It is yet still another object of this invention to provide a "convertible" casing that may find implementation on its own or be the host to an optional guest "biological fluid sensor strap."

It is yet further an object of this invention to provide the consumer with an agreeably soft, sub-divisible and above all, cosmetically appealing "biological fluid sensor strap" that finds its simplicity in the application of one or more transverse folds to a single master cover sheet.

It is an object of this invention to provide mothers with a "sensor" construction novelly made out of a single supporting sheet, that when provided with excised portions of sheet, imparts an hourglass characterization to said sheet for affixing as an optional inner lining to diapers (disposable or washable), or as a pillowing inner lining that becomes intrinsic to other materials positioned flush with the traditional polyethelene sheet which comprises the attribute of disposable diapers.

An object yet further is to provide a novel removably affixable crib death prophylactic device which will detect and alert to the occurrence of urination whenever a suitably adapted guest object, whatever part it may comprise in a diaper's construction, becomes moistened by the manifestation of a liquid or substance of dielectric constant as defined by urine.

An object further still is to provide an adaptable invention that exceeds the precision of prior acquisition, recognition and alarm switching means that may also be incorporatable with prior hardware means, thereby to improve in general the performance of configured means embodied in the prior art.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWINGS

The above-mentioned and other objects and features of the invention will be more fully understood from the following description thereof when read in conjunction with the drawings in which:

FIG. 2a, shows a rendered view of a "convertible" alarm casing that may comprise a two part configuration unitable by means of a dove tailing architecture;

FIGS. 2b and 2a are graphics that show in FIG. 2b an embodiment of RF propagation means comprising in the instant configuration a foldable circuit board, and interrogating appendage that may be positioned within the casing shown in FIG. 2a, or brought out and affixed over the outside curvature of said casing;

FIGS. 2c and 2a are graphics that show in FIG. 2c a general type of removably affixable clasp for temporarily joining said casing shown in FIG. 2a with a garment not depicted;

FIGS. 2d and 2f are graphics that show in FIG. 2d a block diagram of a first alternate fragmented form of a preferred RF style capture embodiment, usable alone or in combination with the ACLS means shown in FIG. 2f, thereby to cause the baby's aspiration modelity to react hypercinesiatic until defeat of the strangle hold that accompanies the onset of a CNS agonal episode derived laryngospasm (SIDS) attack;

FIGS. 2e and 2a are graphics that show in FIG. 2e a removably affixable grating shield suitable for fitting to a provided receptor cavity on the outer curvature of the casing shown in FIG. 2a;

FIGS. 3a and 3b are graphics that show in FIG. 3a a generalized block diagram of a second alternate embodiment of propagation means based on radio telemetry linking and incorporating a self identification feature, and, in FIG. 3b, showing an alternate embodiment of capture means complimentary to the propagation means shown in FIG. 3a, when linking is based on an optoelectronic election;

DESCRIPTION OF THE PREFERRED EMBODIMENT

Figure 1:
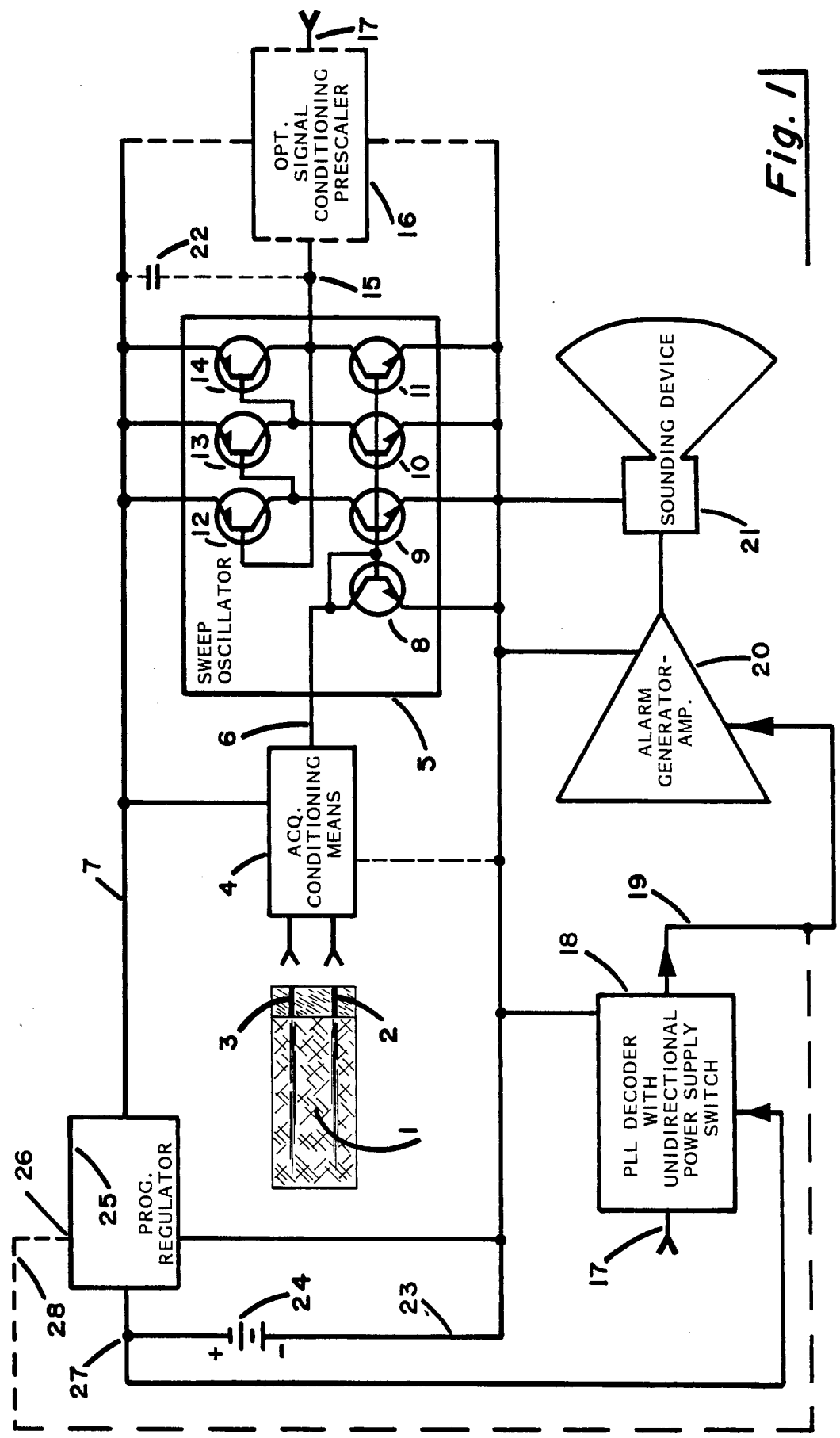
FIG. 1 shows in combination with an optional guest "biological fluid sensor strap" a combination schematic/block diagram of one form of the first crib death prognosticator that actually works.

Although intended to be executed commercially according to features of $I^2L$ or comparable micropower technology, in fact any technology may be substituted in this invention, but should include as shown in FIG. 1, a suitably dress "sensor" comprising a fibrous dress 1 aspected with two coextensive conductive rows 2 and 3 for injecting into an acquisition conditioning means 4 that embraces in the preferred, but not only, embodiment a capacitor free ring oscillator 5 preferably demonstrating an ability to sweep a comparatively wide frequency span pursuant to a ref input 6 change of $\cong 10$ nano ampere while operating down to a V+ voltage at line 7 of 0.7 volts, shown here by way of example comprised of a number of NPN transistors 8, 9, 10 and 11 which bias both the base and collectors of an odd number of PNP transistors 12, 13 and 14, and sourcing its output appearing at 15 through an optional divided-by-N number shaping prescaler 16 into the input of any style of phase-locked loop decoder 18 (by "Samsung of Korea" LM567L (4000 dice per wafer), available), the configuration of which is so arranged, that with it switching means output 19 or the frequency converting decoder 18 only turns subsequent alarm system circuitry 20 and by way of example sounding device 21, "ON," when the output frequency at 15 (or 17) falls within the pre-assigned detection bandwidth of the decoder 18.

Because the dielectric presented by a micturition event by baby materially, notwithstandingly minutely, alters the prevailing dielectrics usually found in the location of interest by babies, consequently, said change in dielectric drives oscillator output 15 to a higher frequency with urine than do other prevailing dielectrics found in and around the traditional swaddling that covers babies.

Given the fact that tests of this embodiment, have by example provided us with frequency sweeps up to 11.00 KHz for various condensations, lubricants and saliva (and incidently also tap water), and for a micturition event in a sweep marking time at 43.00 KHz, it is clear to us that this expanded representation of even the minutest of changes in dielectrics bathing the dress 1 of "sensor" 2 and 3, to be of monumental interest and benefit to a mother's peace of mind and the management of babies' comfort in general.

Owing to the conception of our invention, wherein the tone decoder 18 will refuse to synchronize with any signature frequency less than by the example set forth herein, said benchmark tested 43.00 KHz, we have presented a non-obvious and novel means that will disregard the lower frequency of 11.00 KHz which in this examplary analysis represents all manner of dielectric condensations other than urine. Whereas previous switches including by test the "ubiguitous" National Semiconductor LM 1801 will have preemptively toggelled "ON" at the onset of perspiration, namely, never having reached behind the veil, or if you will, pierced the masking affectation of perspiration mimicking an enuresis manifestation, the present "modulated micturition into diaper detector" means keeps its promise to hold off from switching alarm means "ON" unless and until baby has actually micturitioned.

Whilst the disclosed configuration, or any comparable style of embodiment within the scope of variable frequency oscillator substitution, including function generators or RC means of VCO's (by "Advanced Linear Devices Inc., of Sunnyvale, CA" ALD 555-1 being functional from a supply voltage of just 1 V, available), will give satisfactory "resolution of analysis" as to the condition for which baby is being monitored, those wishing to make adjustment either upwards of or downwards of the disclosed span of sweep by in this example the CCO set forth by way of illustration herein, may do so at (a) the acquisition conditioning means 4 by incorporation of for instance a current regulator diode (by "Ishizuka Electronics Corp., of Edogawa-ku," Tokyo 133, Japan, available), a resistor network, or other op-amp conceptions of modifiable interface in the source bias coupling, (b) by increasing or decreasing the number of transistor pairs in the ring thereby loading with a different storage time constant presented by each PNP transistor added or deleted, (c) by connecting a capacitor 22 across the V+ rail 7 and the output 15 (Observe that the capacitor 22 ought never be connected between output 15 and ground 23, for to do so could result in a high current surge current when V+ 7 is applied to a discharged capacitor 22.), or (d) as previously noted, by interpositioning an oscillator energy shaping network between oscillator 5 and the decoder 18. However, it should be noted that any downward shifting of frequency sweep may require a reconfiguration of the corresponding decoder 18, and also of the skirting of the center frequency to which the decoder 18 will lock, i.e., 14% being normal, and thus may require a trade off of more circuit board real estate than is worth any V+ consumption that may be saved. In any event, battery consumption is not of any major concern because of the rechargeable nature of Ni-Cad or similar power cells 24.

Despite having shown a particularly preferred embodiment of the "modulated micturition into diaper detector," as herein disclosed by specifics of a bare boned example for purposes of illustration of the invention, it should be understood that some potential private label buyers of the modulated micturition into diaper detector may request to have various bells and whistles, modifications or substitutions integrated in or excised from the marketable versions of the present invention. Naturally, accommodation is anticipated and recognized, with all variables of means that indicate themselves suitable included within the scope of the embodiment's embrace, an example of interesting peripheral, not exclusive of other and various possibilities, accruing in the form of one or more chip voltage (current) regulator(s) or multiplier(s) (shadowed in at 25), as may easily be conceptualized in self executing cycles, appropriately interfaced between the power cells' positive d-c power line 27 and the V+ rail 7, wherein as herewith proposed, each such means 25 would be provided with a suitable error flag input 26 (i.e., consisting of perhaps a voltage or comparable sensing means, concurrently provided with a signal delay arrangement (not shown), the whole thereby functioning to disconnect said d-c power line 27 from the V+ rail 7 as in this one of possible instances comprising loads 4, 5, (16) and 18, upon a predetermined stay of instruction execution), so that such input 26 would enable the regulator 25 to periodically be programed to shut itself down upon receipt of an appropriately styled signal, as might be secured from a feed back connection 28 tied into an electrical terminal finding its source of origin at the output 19 of the decoder 18, or someplace elsewhere in the subsequent alarm circuitry 20, all of which would result, practically speaking, in decoupling the d-c power line 27 from cells 24 to said acquisition conditioning 4, oscillator 5 and decoder 18 means, thereby finding its interdiction by 25 from flowing to V+ rail 7, after the decoder 18, by means of output 19, had signaled to said error flag input 26, the acquisition and recognition of oscillator output 15, in such preassigned detection bandwidth, as will have caused tripping "ON," and generation of signal, to and in subsequent alarm circuity 20, consequencing in maximum utilization of d-c power line 27.

If as could occur, the just described mode finds construction by some as overkill, even with a simplification of regulator means 25 by a supplanting with an "FET" switching circuit, or other resetable logic switching interface, including squelch action type bias interdiction means; justification is rational when configured with the interpositioning of a radio frequency link at either of two probable break points located at 19 or 15. Whereas some prior art has disclosed the desirability of a radio frequency linking (see U.S. Pat. Nos. 3,460,123; 3,508,235 and 3,818,468), none has in actuality conceived of a system workable within the real life constraints of feasibility; the object not conceived being that a continuous transmission of unmodulated RF carrier, no matter even if transmitted in a repetitive style of on and off pulsations as suggested in U.S. Pat. No. 3,818,468, possesses any redeemable characteristics under Federal Communications Commission rules and advisories by Direction of the Administrator, or constitutes responsible management of a finite available resource. Also, no immunity from jamming interference in the RF domain results from the teachings in the cited prior art, with false alarms occurring as a matter of conceptualization.

Although our looking glass has touched bases with such proprietary alternate mode alternatives we have developed as by example along the lines of a quasi unterminated low impedance input of a modified high gain acquisition conditioning analog amplifier means, the braodband output noise of which (i.e., white or pink) decreases in a predictable manner upon its input being progressively input terminated by perspiration and thereupon enuresis, thereby when injected forward through an envelope detector shaping network would by reason of threshold differential sampling in associated circuitry, enable a comparator's logic to send the appropriate enabling signal to a tone generator microcomputer IC (i.e., by "Suwa Seiko" or "United Microprocessing Co." of Japan, no U.S.A. equivalent being available), for melodiously indicating (i.e., by means of a Piezo tone transducer as available from "Murata Mfg. Co., of America," or "Gulton Industries, Inc." of New Jersey 08840) when progressive electrical short-circuiting of said acquisition conditioning means' input had consequential to the enhanced quantitatance of an enuresis event, caused sufficient quieting of said acquisition conditioning means' connected analog amplifier's output noise; the lower parts count for microminiaturization, and advantages of lower cost for the measurement of medium of interest offered by herein conceptualization, inclines us, nonetheless, that in the two part embodiments of RF styles of envisioned signal coupling, to advise the user of utilisation of the best mode disclosed in FIG. 1.

With reference to FIGS. 2a, 2b, 2c, 2d, 2e and 2f, and FIGS. 3a and 3b, we have respectively, illustrated two alternate embodiments featuring enlargements of sorts of the basic, best mode disclosed in FIG. 1.

An interested observation will readily reveal that the underlying configuration shown in FIG. 1 is maintained throughout FIGS. 2a, 2b and 2f, and FIGS. 3a and 3b, albeit in proposition of at least two possible fragmentations of the preferred embodiment, thereby suitably arranging for an accommodated linking with magnetic/RF styles of coupling by propagation, and coextensive capture means, or infrared radiation techniques.

Whereas this chapter splits this invention into continuous intensive care and general burst usage models, respectively, this characterized limitation is merely circumstantial for limiting purposes of this paper's volume, and in no way should be construed to be exclusive of any interchangeability of enhancement features that may readily be conceived or practiced by practitioners familiar in practicing the art when once familiarized with the best mode herewith, regardless whether it be in attribute, or in tribute of the fundamental conceptualization of this invention, which by mode, has been demonstrated as previously unenvisioned and unanticipated, and is materially novel in its advancement of the art that is well above and beyond any antecedent reductions to practice in the field of enuresis event reporting systems.

With reference to FIGS. 2a, 2b and 2d, we show a first and a second structure comporting in general to a propagation 100 and capture means 200 catering to a modulated micturition into diaper system. Although no specific shape is delineated for either said propagation 100, or said capture means 200, it is clear that said means ought to be based upon a minimum of volume so as not to be obstructive in their employment by mothers or nurses. However, for said propagation means 100, a pleasant configuration might nonetheless be as envisioned in FIG. 2a, wherein not unlike that one popularized by ladies' powder compacts of years yore, there is included an upper 101, and a lower 102, cavernous housing symbolic of the powder and puff bay in the lower wing, and the reflective mirror bay in the upper wing, of a lady's folding compact; each of said first 101, and second 102, respectively independently sealed off housings being hinged together with a foldable or pivoting means in the general area at 103, as makes permissive said housings 101 and 102 to be folded or fitted captively to each other or optionally releasably fitted into each other with any manner of conceivable retaining means (not shown), or be conceptualized to function as an articulatable receiver for purposes of thereinbetween mechanically and electrically removably vising on to one end of an optional guest "biological fluid sensor strap", the combination of said independently partitioned cavernous structures thereby providing a single interactive unit when assembled around, for example as shown in FIG. 2b, a unitary or two part interconnectable hourglass shaped flexible printed circuit board 104, flexibly hinged over at 105, which can include being appropriately dressed and embodying conductive screening means with alternating hot melt insulating ink and hot melt type graphite electroconductive ink as available on a strip-away polyester base film (i.e., by "Elform" of Reno, Nev. 89510), to communicate electrical power 106 and ground 107 between a removably installed energy cell 108 positioned through a closeable opening (not shown) provided to one of said cavernous structures, preferably 102, and a coextensive surface mounted VLSI circuitry 109 comprising in like and kind such antecedently described modulated micturition into diaper detector means as might by way of the example herein embrace a microprocessor cycled power line regulator with interrupter flag inputs and outputs 110, an acquisition conditioning cum sweep oscillator 111, a modulation accepting RF transmitter 112, and an endorsed aerial means 113 originating at the output of said transmitter means 114, the whole VLSI 109 as such being conveniently positioned inside of the opposite one of said cavernous structures, preferably 101. To secure an externally accessible means whereby accessories could be connected to propagation means 100 to intercommunicate with the area of measurement of interest being interrogated by suitable "biological fluid sensor strap," or indeed directly by unit 100 itself if accordingly conceptualized, thus to enable a wide variety of handshaking with said in cavern enclosed circuitry, we propose connecting at 115 a "flexible circuit heat seal connector" appendage flapper 116 (by "Elform"), for purposes of extracting through the back plate of caverns 101 and 102 to its exposure and utilization necessary first 117 and second 118 "sensor" tracers intrinsic to said acquisition conditioning input 119 and 120 situated on circuit board 104. Obviously, circuit board 104 could itself provide such an appendage if accordingly conceived. To wit, tracers that may be thereby arranged to extend outward onto the place 123 from within either of said cavities 101, or 102, so as to enable their being affixed by means into place snug to either one of the outside surfaces at 121 or 122 as these surfaces are located opposite to each other in the place 123 constituting said vising area where housings 101 and 102 flatten against each other when flush; or when adequately lengthened at 124, can be folded back upon itself at 124 over the outside circumference of either of said housings 101, or 102, at 125 or 126, respectively, and thereupon easily be affixed laid down on either of said outside curvature(s) 125 or 126; or simply be brought out of any cavity of interest to self same cavity's overt surface of curvature by suitable means of trespass and affixing by means in place, or indeed, by any or other of surrogate mechanical and electrical means for purpose of interfacing with an enuresis event. It will thus be understood that said single interactive unit 100 comprising 101 and 102, when used by itself, can simply be popped into the space in between baby's skin and the swaddling wrapping around baby's bottom, or, if employed with the optional "biological fluid sensor strap", with or without affixable gripping section, be removably affixed to some outer garment, or even the swaddling itself, by means of by example, clasp 127 as shown in FIG. 2c, that may be removably fitted to unit 100 by provision of any derivative of the depicted periclasping extension(s) 128 and 129, that may be keyed to fit one continuous or two companion key way receivers at 130 (and 131) girding unit 100.

Following through with but one example of the RF conception of envisioned modulated micturition into diaper detector signal coupling means, receiver housing 200 as shown in FIG. 2d, would preferably include an aerial 201 feeding the capture of the modulated, ergo, coded transmission into a monolithic radio IC 202 (i.e., by "Telefunken GmbH of D-7100 Heibronn, West Germany" U 4062 B being particularly well integrated, stable and of low noise type), the output of which 203, after its demodulation and conditioning according to desire, is transferred forward to the input 204 of a monolithic single chip phase-locked loop tone decoder (i.e., by "Exar Corporation of Sunnyvale, CA 94088," XR-567), which is tuned to activate its output current steering switching means upon the detection of and comparison with an internally pre-designated frequency, all consequencing, as it will, in any concurrence of the externally introduced and internally generated frequencies thus indicating to the decoder IC 205 the occurrence of a micturition event at the propagation means 100, and therein constitute an order to the switching means of decoder IC output 206 of capture means 200, to sink an electrically connected alarm device 207 or other senses stimulating means in a load current of up to 100 mA without the addition of any additional peripheral, save of course for an electrical energy source as may be any type of an interruptably sourceable direct current means 208.

Whilst undoubtedly it may to some also be of interest to know at all times as to whether moisture as distinct from an enuresis event exceeds nursing criteria for the confines constituting that immediacy located at the touching of baby's skin by swaddling means clothing the baby, realization is available, simply, and cost effectively, by nothing more than the addition of a second tone decoder 209 for instance, of like and kind as primary tone decoder 205, and providing second decoder 209 with its own attention getting means 210, ergo, said second decoder's input 211 being connected in like and kind manner to radio output 203 as the primary decoder 205 but distinguished by having its internally pre-designatable PLL generator frequency so tuned as to coincide with such lower frequency, which propagation means 100 makes representation of, upon sensing the occurrence of perspiration across the propagation means' acquisition conditioning means.

As a further enhancement of our system, we also anticipate that a perhaps removably fittable grating shield 132 as shown in FIG. 2e, be attachable to or integrally incorporated with the outer curvature 126 of suggested propagation means 100, thereby to befit purposefully the emplacement of said lengthened flapper 116.

Notwithstanding no specific shape having been delineated in the accompanying drawings for the capture means 200, any portable shape may of course be adopted. However, we profess having achieved especially good results by conceptualizations that include having said RF capture aerial 201 or infra-red receptors, and in fact the entire capture means 200, be removably built into or comprising an integral part or structural member 415 of any baby crib, any baby stroller, any infant's playpen 416 or dislodgable constraining and specialized furniture in general.

FIGS. 3a, and 3b, reallege in block diagram graphics, most of the features previously asserted in FIGS. 1, and 2d, but now incorporating a modified special feature in the form of a different circuit splitting arrangement which may be used with any style or number of circuitries of addition or the embrace of an optionally shown self-identification feature for utilization in the field of employment such as in crowded nurseries, post surgical stations, or in health care wards tending to the specialized needs of the geriatrically needy.

Once again we reiterate a propagation means 300 as shown in FIG. 3a, and a capture means 400 as shown in FIG. 3b, as co-relate to antecedently nominated means as shown in FIGS. 2b, and 2d, respectively, although in the forthwith configuration, propagation means 300 (100) does not propagate, as hitherto disclosed, as the result of the propagator's carrier frequency means (113) being modulated by the acquisition's sweep generator output (112), and thus the propagated signal (114) being a reflection, in real time, of the actual modulation product occurring as a direct and proximate result of the medium encountered either directly (116), or indirectly (via optional "biological fluid sensor strap"), by the acquisition conditioning means (111), and concatenately, the extracted band of frequency signal processed by the capture means (202) being limited only by the number of separately tuned decoders (205, 209, etc.) branched to the receiver's demodulator output (206) (a frequency counter with digital display substituting for frequency tuned decoders being a matter of personal preference and ability to pay for its increased cost), but instead is limited to propagating the issue of a micturition event pursuant to a conception idealized not in particular for single units intended for use in a home or apartment environment, but rather for institutional usage where multiple units are expected to function in close proximity to each other as would be usual in multiple bed wards where patients are bedded in close adjacency to each other, and the units as shown in FIG. 3b by the letters "A" and "B" therefore needing conceptualization with a self identification feature which would draw attention to the particular unit calling attention to itself.

Walking the block diagram graphics of FIG. 3a, we show a modified propagation means 300, that is characterized by embodying a "biological fluid sensor strap"

301 connectable acquisition conditioning means cum sweep oscillator assembly 302, the conditioned output of which 303, is electrically connected to the input 304 of a signal converter means such as a heretofore illustrated embodiment in the style of a pre-tuned monolithic single chip PLL tone decoder 305 (or as is shown, an A/D decoder interfaced with a logic compatible gate switch by way of example), the logic output of which 306, upon its activation in the presence of a micturition event occurring across sensors 307 and 308 connected to the "biological fluid sensor strap" 301, transfers electrical current to both the Volts connection 309 of a programmable monolithic sign generation IC 310 perhaps of the DTMF variety (in all likelihood any CMOS LSI version of the venerable MM53120N by National Semiconductor of Sunnyvale, CA 94086), and the Volts connection 311 of a (300 Mhz–800 Mhz), suggestive, RF carrier generator 312 whose in feed 313 is connected to the data out terminal 314 of IC 310. With reference to FIG. 3a, there is also illustrated an antenna 316, and a DC source of electrical potential 315, perhaps a rechargeable lithium power cell by "Moli Energy Limited of Burnaby, B.C. Canada V5C 4G2," the power of which may be regulated and incorporate or have incorporated with it, a delayed power down feature that self-activates after, for instance, the appearance of substantial potential at decoder output 306.

Although the capture means 400 as shown in FIG. 3b, will always be characterized "programmed" in a compatable mirror image of the by example proffered propagation means 300 as previously shown in FIG. 3a, any system as would be selected needs not only to be practiced according to personal preference, but also to be based upon the radiation limitations imposed by the governmental regulations enacted by the agencies functioning under the jurisdiction and laws of the particular country to which we will export our invention. Therefore, any substitution of wireless linking means that gives the same "indivudual code programmable" result between individual unit pairs such as the by way of example available means of a comparator designed to listen for a magnetic signal emitter as is available through "Dallas Semiconductor", of Dallas, Tex. 75244, is both conceived and readily achievable, "including by DTMF means or in its simplest form, by means of "Pulse Position Modulation" (PPM), as is usable with or without a carrier frequency. A case in point being, when in response to the propagation means 300 having comceptually been outfitted with a 32 or more code PPM (ultrasonic or) Infra-red LED transmitter and diode (i.e., substituted for 310 and 312, respectively, by a "Plessey Solid State of Irwine, CA 92714," SL490), the capture means 400 correspondingly embraces as (ultrasonic or) Infra-red diode or phototransistor array receiver 401 (e.g., by "Texas Instruments of Dallas, " Tex. 75222), that is plugged into the (differential) input stage 402 and 403 of a dedicated preamplifier IC 404 (by "Plessey,"e.g., SL486), the output 405 of which interfaces with the input node 406 of a preferably latched output, code demodulating receiver IC 407 (by "Plessey," e.g., ML928/9). Of course, pursuant to preference or due to noise considerations, each diode may be provided with its own input stage, the outputs of which if such be the case might then have their outputs 405 et al., combined together at the input 406 of the demodulating receiver IC 407. Further still, in larger units, inputs could be individually connected, in which case, a sequential strobing of the inputs to IC 407 could be accommodated. Customer and market place response will at all times dictate each country's preferred means of alarm 408 connected to the open drain drive outputs 409, 410, 411, 412, et seq., of 407, and may conveniently be a directly driven nurse station console mounted LED array, each single LED 413 being dedicated to signal the propagation of one of the several propagation means 300 in the system, or in fact any other alarm means permitted to function in each country. In the operation of capture means 400, rectified AC electrical power would be the electrical potential of choice for fixed station operation. Portable variants on the other hand, would find a (rechargeable) battery source 414 more advantageous. It should be appreciated that the foregoing examplary circuit components and values as given for the circuits of FIGS. 1, 2b, 2d, 3a and 3b, are for purposes of illustration only and to more particularly describe the nature of our conception and conceptuallizations—and are not intended as a limitation to for example utilization in numerous other applications requiring the herein expoused attributes. It should also be clear that whereas such arrangements have particular utility as a crib death (SIDS) warning device, it wll be apparent that numerous other arrangements and modifications may be devised and made by one skilled in the art without departing from the spirit, essence and scope of the posit invention.

Figure 4A:
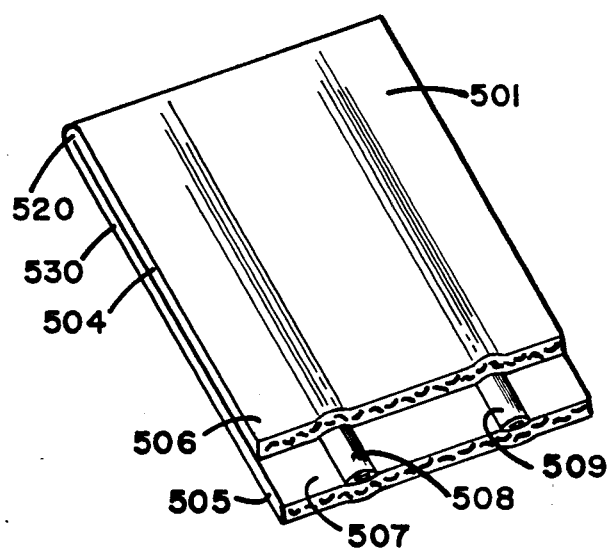
FIG. 4a, shows a view of a preferred "biological fluid sensor strap" featuring a novel transverse fold architecture resulting in a manner to create a terraced affect at the edge opposite to said fold.

Referring to FIG. 4a, we show a novel means for constructing the antecedently mentioned optional "biological fluid sensor strap." To address the need for an inexpensive, easily manufactured strap, marketing considerations told us to never lose sight of the imperative that any strap manufacturing be limited in the amount of material triming operations needed, to result in a marketable product. As shown in FIG. 4a, the objective was achieved by the non-obvious means of novel conception wherein with the application of a single transverse fold to a square area of sheet, there results a biological fluid sensor strap that may be packaged for the consumer in a number of ways, including as an individual strap, in a bulk configuration permitting a strap by strap acquisition by the consumer, or a strap of enlarged surface area thereby to permit its addition to or substitution in place and stead of a conventional diaper's inner fibrous, non-woven web lining, either by the consumer, or a diaper manufacturer.

More specifically, with the sensor unit shown in FIG. 4a, we outline a moisture-permeable porous sheet 501 that by reason of being folded over upon itself at the transverse fold 520, provides a first 530 and second 504 layer construction and a terraced effect at the edge opposite to said fold 502. As will be noticed, the transverse fold 520 is arranged in such a manner that the second layer 504 extends away from the fold 520 for a distance that is shorter than the length away from said fold 520 provided said first layer 530. The reason that a peculiar length of layer 530 comprising coextensive layer 505 is configured to extend beyond the edge 506 of layer 504 resides in the fact that the resulting exposed inner surface 507 of layer 505, provides a convenient manipulatable platform pursuant to which, it makes possible to easily inject directly (or perhaps via an optional reuseable affixable gripping interface connector means) the "by fold held captive" connectors 508 and 509 into said appropriately styles spaced 123 of FIG. 2a, or in fact any other similarly dedicated port or mating feature, there to electrically and mechanically mate with the interrogating "sensor tracers" 117 and 118 of appendage flapper 11b as are intrinsic to said acquisition conditioning input 119 and 120 situated on circuit board 104. As will be understood the vising together of cavernous structures 101 and 102 thereby completes the depicted propagation means 100, means by obviating any need to pierce any layer of the guest "biological fluid sensor strap."

The means, to keep affixed or fused to each other said touching layers 530 and 504, can of course be in any configuration found convenient, and includes in its embrace wherein there is interleafed between layers 530 and 504, a plexus of poly-film or of substantially equivalent material, the instant variation providing for an economical assembly, whereby said comparatively low melt plexus establishes an adhesive agent when layers 530 and 504, are passed between heated pressure (optionally textured) rollers during this one of numerous possible variations on a process of manufacture. Naturally, a mulch of interwoven or predispersement of plexus derived fibres in a resultant special variation on the ubiquitous non-woven fiberous inner lining cloth commonly employed in the manufacture of disposable diapers would obviate said propounded interleafing and is in fact envisioned when the quantity warrents its special manufacture. Symbiotic, the conductors 508 and 509 should preferably be made of a non-rigid material, and may be slightly adhesive or made adhesivable to an adjacent or proximate surface by any configuration or intermediary means disclosing itself convenient including heat or/and pressure sealing.

Figure 5:
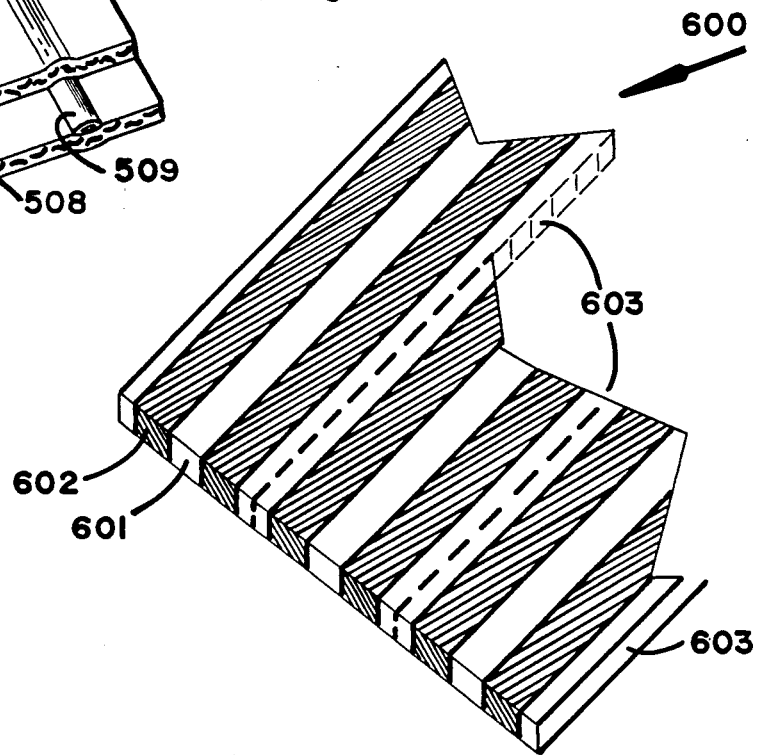
FIG. 5 shows an alternate configuration of a preferred "biological fluid sensor strap" of wipable architecture that may find its embodiment aspected with a fibrous dress featuring the novel transverse fold and pull off tabs as shown in FIGS. 4a, 4b and 4c.
Figure 4B:
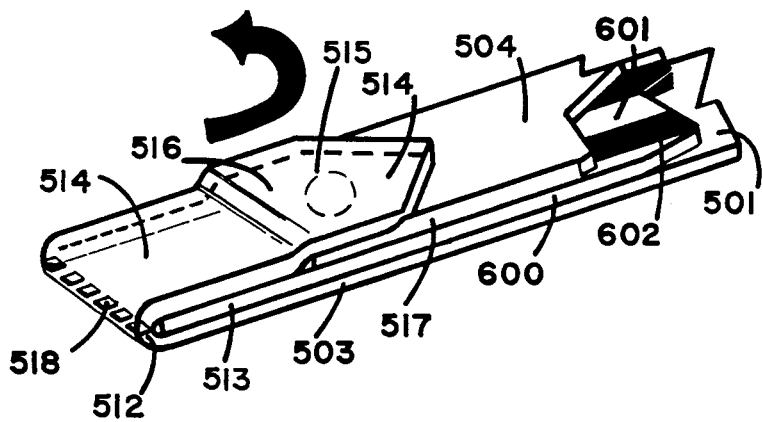
FIGS. 4b and 4c, with reference to FIG. 4a, demonstrate additional dressing configurations for said optional "biological fluid sensor strap" comprising pull-off tabs which upon tearing off, as facilitated by perforated provisions, reveals said terraced effect shown in FIG. 4a, a configuration also suitable for conceptualization with a two ply co-extensively superimposed architecture.
Figure 4C:
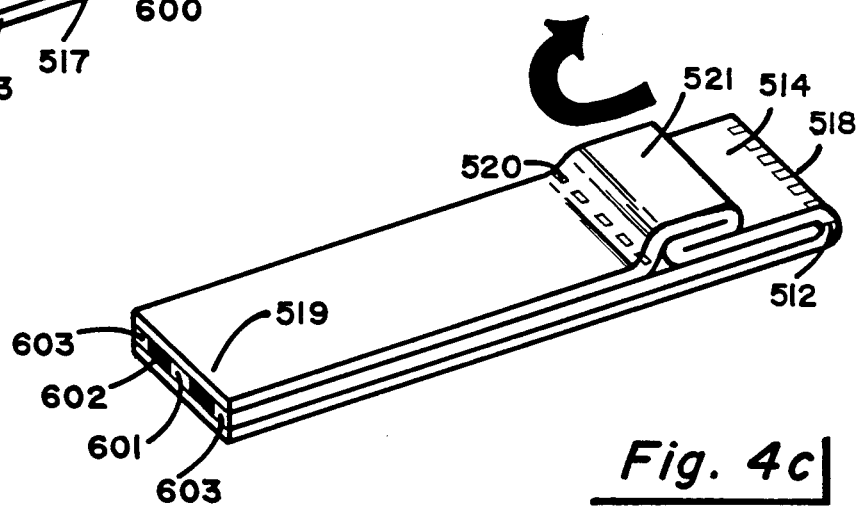

Although cost effectiveness considerations might support and argument that the best mode for the optional biological fluidm sensor strap would possibly reside in an undressed construction which implies a wipeable, to wit, reuseable configuration as would present itself as an unclothed arrangement as shown in FIG. 5, wherein a construction is envisioned comprised of a means of general equivalence or couched in terms of a fused/vulcanized mat 600 consisting of multiple rows of another or a hot melt non-conducting insulating ink means 601 alternating with another or a hot melt conductive graphite material means 602, said mat being flexible, said mat further being provided with longitudinal scoring lines 603 down the center of alternating rows of non-conducting insulating material 601 thus to provide a built-in shearing means to assist with user in securing for him or herself a portion of the mat 600 consisting of a central unscored length of non-conducting material 601 shouldered on opposite edges of 601 by two conductive graphite material lengths 602, it is more probable that the affluent user would elect to use the means in FIG. 5 clothed in a variation on the dressed construction propounded by FIGS. 4b and 4c herein. Naturally, the scoring or perforated feature 603 would then also find its shearing compliment incorporated to porous sheet 501.

It should further be understood that touching layers 530 and 504 may also be fabricated in an oversized configuration thereby to emulate the traditional dimensions necessary to enjoy its substitution in place and stead of such moisture-permeable porous facing sheet which is substantially coextensive with the moisture-impermeable backing sheet material which forms a disposable diaper's outside surface. Said oversized configuration furthermore being packageable as autonomous diaper liners.

It is still further contemplated, that in the scope of this invention, the conductive means 2, 3, 117, 118, 508, 509 or 602, need not necessarily be exclusive of any specific style or number of developing electrochemical conducting polymerizations employing ion insertion (doping) during the anodic oxidation for the generation of stable conducting polymers or conductive polymeric coatings, or fiberized means endowed or enhanced with a nickel or silver-loaded like electroconductive carrier finish. Other electroconductive embodiments applied by option of sputtering, vacuum-deposition, or manufactured by surfacing with a silver-loaded electroconductive finish either in commonality or indeed in bilateral dissimilarity, split between means 508 and 509 (e.g.), thereby to galvanically assist in driving said acquisition cum sweep generator 4, 111 or 302, are embraced configurations within the envelope of this invention whenever it be found convenient dependent upon the specific generator's acquisition guard, or sensitivity, pursuant to interrogated developments therein. Different packaging styles of the optional biological fluid sensor strap are also contemplated whenever convenient, and may include mat 600 and/or sheet 501, or any mutation thereof being pre-sheared for the consumer into singly manageable straps. A still further enhancement to pre-sheated biological fluid sensor straps is shown in FIGS. 4b and 4c, where a novel removable contamination deterring flap 514 with integral pull tab, are shown fashioned from an unbearing extension of moisture-permeable porous first layer 530 that as shown in FIG. 4b, is provided with a second fold 512 commencing at the transverse edge 513 where non-conductor 601 and conductors 602 terminate, and there be folded over to provide a third layer 514 brought down to bear over non-conductor 601 and conductors 602, and a portion of second layer 504. Means for temporarily affixing third layer 514 to second layer 504 can be of any variety including a drop of adhesive applied at the touching of layers 514 and 504 at 515, or by crimping together at the edges 516 and 517. Application of a perforated tear line 518 to the un-sheared moisture-permeable porous sheet 501, in the location of the second fold 512, prior to sheet 501 being dressed to mat 600, will afford a simple disengaging feature for the user after peeling back third layer 514 from the assembled strap. In FIG. 4c, we show in substance as depicted in FIG. 4b, with the substitution of a but cut 519, the addition of a second perforation 520, and pull loop 521, that may be laid down upon layer 514.

Although the benefits of having an accurate crib death (SIDS) warning device will not be lost on anyone who has witnessed the trauma that results when parents recriminate themselves upon having suffered the loss of what was perhaps an only child, to sudden infant death syndrome, we continue to clinically evaluate means whereby to avert sudden infant death syndrome from taking its course upon the onset of what is nothing less than a bizarre paroxysm of asphyxiation through hypertonicity, in particular, should it happen that any one of the numerous types of alarm means that may have been outfitted to any one of the output nodes of any one of the various decoder means having worked correctly, nevertheless failed to timely catch the attention of supervising staff or one of the parents; e.g., mother having been deafened by the whirr of the electric vacuum cleaner, or perhaps been distracted by a neighbor's call, and thus resulted in what otherwise could have been an avoidable fatality.

In the past, numerous efforts have been undertaken to surrogate the need to personally monitor baby at all times. Of the most prevalent types of baby sitters are "The Gerry Intercom" of U.S.A., the "Playskool" portable listening system and "The Mothercare Baby Alarm, model 7972" of Great Britain, type of means, whether hard wired or RF linked, as in the characterization of the hospital white embodiment of the Sony brand "Babycall" elecronic babysitter, another means that like the aforementioned styles, is ordinarily consisting of a sending means embodying at least one sound transducer means and transducer's signal transmitting means and a companion receiving means that embodies an amplification means that outputs into a signal indicating means, so as to let mothers by way of a remote microphone in baby's room presumably hear all necessary signals eminating from the nursery area. But the alleged peace of mind thus promised, is substantially deceiving, this the result from a tragic miscomprehension of the syndrome for which the mother seeks to monitor, because a SIDS related death, events rather silently without a cognizable outcry by baby. A striking feature which is supported by a major Seattle study in which not one SIDS case was observed to die. In other words, every single case was discovered lifeless after failing to awake from a nap. Although seventy-four percent of babies discovered decreased are found to have expired between 06:00 A.M. and 12:00 noon, but mostly between 07:00 A.M. and 09:00 A.M., with 16 percent found to having succumbed towards the evanescence of the 12:00 noon to 06:00 P.M. time frame that is to say, well within the watchful hours of the day, it is nevertheless a act, that without regard to a mother's best past efforts, including investing with "The Gerry Intercom" type of means, such efforts have proven unsatisfactory, wherein crib death, continues to unabatedly strike down babies.

Of the numerous interconnections that we have investigated, including electrically packaging the entire capture means as an integrally configured part of components existing in baby's room listening device systems or the alarm output of alarm means 20, or 207, or 31b, or 408 into the microphone's signalling circuitry of such monitor means as "The Gerry Intercom" by an embodiment wherein the capture means is impaired means functionally arranged as a sender's means or trunking the output of capture means 200, or 300, or 400 to react into any of the numerous types of anti-burglar circuitry usually installed on premises whereby are activated house lights into a flashing or an otherwise convenient mode, the best mode interrogated, nonetheless, appears to be one that is contemplated to be procurable only pursuant to a doctor's prescription for those cases that lodge in the high risk category (Male Caucasian, Female African American) or having exhibited a genetic predisposition (Male Asiatic Indian) or a medical history of crib death susceptibility.

The resuscitation support system 212 as shown in FIG. 2f, of choice, is a task scaled adaptation of any convenient cardioverter style means 213 that finds its electrical operation defined and programmed by a ported 214 microprocessor means 215 that has one of its inputs connected into a decoder's output node 206, as shown in FIG. 2d. As shown in FIG. 2f, the means employed in the resuscitation support system 212 is configured so that induction of tetanic contractions in offending muscle by electrically stimulated reflexive hyperdistention, administered in successively augmented dosages to baby by way of perhaps an expandable belt means comprising electrodes 217 and 218, causes baby's aspiration modelity to react hypercinesiatic until defeat of the strangle hold that accompanies the onset of laryngospasm (SIDS). In promotion of minimal circulatory flow to the brain until medical attention arrives, we provide an IR illuminated photoelectric monitor head 219, or already known configured, configured to supply the necessary cardiac information to the microprocessor 215. In using the present invention, the aforementioned IR pulse monitor head 219 (or any other type monitor for that matter) is removably secured to perhaps an ankle or toe of the baby so as to allow its detecting part to send an appropriate representation of the baby's pulse to the designated diagnostic input 220 of the microprocessor 215.

Normally the microprocessor 215 will merely average, over a recurring time base, the number of pulses received from baby, and except as a last resort in the absence of a complete cessation thereof, will abstain from instructing the cardioverter 213 to activate its life support function in support of tetanic convulsion.

If on the other hand baby should begin to suffer from an acute onset of a CNS agonal episode of self destructive motor activity (a precurser to crib death), the occurrence will not escape the microprocessor 215 which under its operational architecture will have picked out this trend out of the pecularity of signal that a baby's pulse exhibits as a consequential stress syndrome of increased negative intrathoracic pressure (SIDS), and responsively, will as a preparatory measure, key-up the cardioverter 213 to stand by mode.

If baby's condition was transitory as is possible by reason of failure to mature, and in fact should subside, the operational architecture will instruct the microprocessor 215 to stand down the cardioverter 213, however it be configured.

If the baby's unassisted fortitude failed to overcome or break free of the grip of increased intrathoracic pressure, the microprocessor 215 according to the operation architecture being run, will consonant with whatever mode configuration is prescribed by the doctor, repeatedly prospect its input for an occurrence of a micturition event, subsequent to the manifestation of which, i.e., at node e.g., 206, will thereupon enter into an "on hold" mode for an optional (by thumbwheel 221) predeterminable interval of time, this provision being offered so as to provide a mother or health care person with the opportunity to personally respond and intervene resuscitatively as to the baby's care upon having head or seen the provided alarm means e.g., 207, thus to create the opportunity to choose, whether to elect for an instruction instructing the microcomputer 215 to power down the cardioverter means 213 and personally assume the responsibility for applying spasm countermanding cum Cardiovascular Pulmonary Disfunction Resustitation (CPR), or to stand by whilst the cardioverter 213, upon prompts harmonious to pulmonary signals 220 emanative the IR monitor 219, seeks to "wake-up baby from its nap" through induced compression reflex to electronically dislodge the increased negative intrathoracic pressure that underlies the suffocation of baby (i.e., crib death never occurs when baby is awake), a further benefit of which, clearly would be the emancipation of the attending person to reimplement the breathing of baby with a safe dosage of perhaps a gaseous supplement in furtherance of Advanced Cardiac Life Support (ACLS) performance.

In the event that the interlock afforded by said "on-hold" mode is not by-passed, whether because of choice or because the presence of mother is not available to manually abrogate the resuscitation performance, it is an object that with the stabilization of pulmonary signals across diagnostic input 220, the microcomputer 215 will assume the crisis to be over and stop intervention treatment.

Notwithstanding that we recognize that to some people the discussed course of hyperemotivity might sound anguishing, it should be remembered that the difference as a result of treatment to that one of treatment withheld being the difference of a baby saved against that of a baby died, respectively.

For those persons who still believe that the course of treatment does not justify the inflicted (albeit temporary) dirigomotor of baby, it should be remembered that neonatal surgery is performed routinely on babies without anasthesia of any kind in the interest of saving the lives of babies who otherwise would have to be left to die untreated.

Whereas cardioverters have at some time or other over the years appeared in various guises from the ubiquitous clinical cardiac defibrilator dedicated addressive to vivifrying to normal the sinus rhythm turned absent due to cardiac arrest or arrhythmias such as ventricular fibrillation, to miniaturized microphone operated electronic snore or dog bark depressors as taught in U.S. Pat. Nos. 3,025,858 and 3,480,010, and conceived to inflict discomfort for discomfort's sake, none of the prior art has appreciated it to be conceivable to devise a prophylactic means in quasi mimicry of the "Heimlich Maneuver," acting concordantly with a novel veritable means for the detection of an agonal episode resulting micturition event, thereby singly, or in combination, to challenge and overcome the majority of crib death mortalities, and even in the higher age group of Asian men who it has recently been discovered are given to suffer death from Sudden Infant Death Syndrome affliction.

Having expressed particularly preferred embodiments of the invention as hereinbefore disclosed in detail for illustrative purposes, it will be recognized that variations or modifications of the disclosed apparatuses, including the arrangement, order or choice of parts, all lie within the scope of the present invention.

The term "sweep oscillator" s used in this invention broadly refers to any suitable function generator permissive its adaptation to ramp in response to contact with various bodily fluids.

The term "acquisition conditioning means" as used in this invention broadly refers to any suitable circuit configuration adoptable to the circumstance and performance considerations of employed function generator and further does not exclude as permissive of adaptation to cohere, an amplifier, op amp or configuration having its differential inputs coupled so that one input is sourced by a ref voltage forced through its other input.

The term "phase-locked loop tone or frequency decoder" as used in this invention broadly refers to any suitable decoder means and further does not exclude as permissive, substantially equivalent unspeced A/D (for DAC) to comparator patched trigger logic derived indicator enabling microcomputers or analog peak rectified pulse integrated responding op amp sourced indicator means, or modulo-K counter digital PLL IC's (by RCA of Somerville, N. J. 08876), as could feed by relay sourced secondary e.g., telephone auto-dialing 222 or other alarm means, either solid state or traditional, with or without resetable latching means.

The term "hot melt type ink" as used in this invention does not exclude substitution with equivalent means, including conductive elastomer means, all being permissive of adaptation theby to elongate a portion or portions of circuit board into reach of and interrogation of the measurement area of interest.

The term "casing" for propagation means as used in this invention broadly refers to any portable casing means permissive its adoption to encase one or more of the novel features which are embraced by this invention.

The term "propagation means" as used in this invention broadly refers to amplitude, frequency shift, digital pattern, ultrasonic and infra-red transmitting means, both with, and without a carrier frequency.

The term "demodulator" as used in this invention broadly embraces discriminator, detector voltage multiplier, and digital level BCD means.

The term "demodulator casing" as used in this invention includes cribs and other baby furniture means.

The embodiments of the invention in which an exclusive property or privilege is claimed are defined as follows.

We claim:

1. An apparatus for specific fluid detection in prophylactic prognosis of a medical condition known as Sudden Infant Death Syndrome, comprising:
   a suitable biological fluid sensor for receiving and transmitting the manifestation of micturition;
   a casing for suitably clamping to said sensor and establishing electrical contacts with an embodied acquisitioning means adapted to driving a variable frequency oscillator to the signature frequency of a manifestation of micturition; and
   a signal converter means configured for specific frequency recognition that is receivably connected to said signature frequency in a manner that upon variation of frequency by said oscillator to said signature frequency as a result of said sensor receiving the manifestation of micturition in precursor to a CNS agonal episode derived laryngospasm attack there results the orgination of a transition by a switching means the performance of which is bi-directionally spliced firstly for the operation of a means comprising a stimulating alarm system and secondly for initiating the tasking of a multi-ported microprocessor that controls an ACLS means operationally architectured to induce increased negative intrathoracic pressure relief when not cancelled by supervising personnel or the microprocessor itself upon accessing the receipt of data that is comprised of co-processed signals.

2. An apparatus for specific fluid detection in prophylactic prognosis of a medical condition known as Sudden Infant Death Syndrome, comprising:
   a suitable biological fluid sensor for receiving and transmitting the manifestation of micturition;
   a casing for suitably clamping to said sensor and establishing electrical contacts with an embodied acquisitioning means adapted to driving a variable frequency oscillator to the signature frequency of a manifestation of micturition;
   a modulation accepting propagation means connected into the output of said oscillator; and
   a second portable casing with embodied capture means the output of which into a signal converter means that by its configuration for specific frequency recognition of such signature frequency as announces the event of said sensor having manifested a micturition in precursor to a CNS agonal episode derived laryngospasm attack is conceptualized to result in the origination of a transition by a switching means the performance of which is bi-directionally spliced firstly for the operation of a means comprising a stimulating alarm system and secondly for initiating the tasking of a multi-ported microprocessor that controls an ACLS means operationally architectured to induce increased negative intrathoracic pressure relief when not cancelled by supervising personnel or the microprocessor itself upon accessing the receipt of data that is comprised of co-processed signals.

3. An apparatus for specific fluid detection in prophylactic prognosis of a medical condition known as Sudden Infant Death Syndrome, comprising:
   a suitable biological fluid sensor for receiving and transmitting the manifestation of micturition;
   a casing for suitably clamping to said sensor and establishing electrical contacts with an embodied acquisitioning means adapted to driving a variable frequency oscillator that is connected to a signal converter means in a concept that functions to transition a switching means into energizing a modulated propagation means when said sensor upon having manifested a micturition event in precursor to a CNS agonal episode derived laryngospasm attack has prompted said oscillator to react with a signature frequency characteristic of micturition manifestation and said signal converter in reaction thereto originated the transition of said switching means into energizing said propagation means; and
   a second portable casing embodying a capture means connected to a compatible signal converter means that is conceptualized upon mirror image modulation acquisition to result in the origination of a transition by a switching means the operation of which results in a bi-directionally spliced signal flow firstly for directing into operation a means comprising a stimulating alarm system and secondly for initiating the tasking of a multi-ported microprocessor that controls an ACLS means operationally architectured to induce increased negative intrathoracic pressure relief when not cancelled by supervising personnel or the microprocessor itself upon accessing the receipt of data that is comprised of co-processed signals.

4. An apparatus for specific fluid detection in prophylactic prognosis of a medical condition known as Sudden Infant Death Syndrome, comprising:
   a suitable biological fluid sensor for receiving and transmitting the manifestation of micturition;
   a casing for suitably clamping to said sensor and establishing electrical contacts with an embodied acquisitioning means adapted to driving a variable frequency oscillator that is connected to a signal converter means in a concept that functions to transition a switching means into energizing a code modulator means and a thereto connected coded modulation propagation means when said sensor upon having manifested a micturition event in precursor to a CNS agonal episode derived laryngospasm attack has prompted said oscillator to react with a signature frequency characteristic of micturition manifestation and said signal converter into energizing said propagation means into propagating coded modulation; and
   at least one portable casing embodying a capture means connected to a compatible signal converter means that is conceptualized upon coded modulation acquisition to result in the origination of a transition by a switching means the operation of which results in a bi-directionally spliced signal flow firstly for directing into operation a means comprising a stimulating alarm system and secondly for initiating the tasking of a multi-ported microprocessor that controls an ACLS means operationally architectured to induce increased negative intrathoracic pressure relief when not cancelled by supervising personnel or the microprocessor itself upon accessing the receipt of data that is comprised of co-processed signals.

5. An apparatus for the remote sensing of a micturition manifestation in the space between the outer surface of swaddling and the swaddled, comprising:
   a suitably prepared biological fluid sensor for receiving and transmitting the manifestation of micturition;
   a casing for suitably connecting to said sensor and establishing electrical contacts with an embodied acquisitioning means adapted to driving a variable frequency oscillator to the signature frequency of a manifestation of micturition;
   a modulation accepting propagation means connected into the output of said oscillator; and
   a portable second casing with embodied capture means the output of which into a signal converter means operates in a concept that functions to transition a switching means connected to said signal converter into switching on an alarm configuration that injects its characteristic modulation into the signal circuitry of a baby listening device after said capture means' acquisition and said signal converter's having sampled and found the propagated oscillator's frequency to be representative of a manifestation of micturition signature frequency.

6. An apparatus for the remote sensing of a micturition manifestation in the space between the outer surface of swaddling and the swaddled, comprising:
   a suitably prepared biological fluid sensor for receiving and transmitting the manifestation of micturition;
   a casing for suitably connecting to said sensor and establishing electrical contacts with an embodied acquisitioning means adapted to driving a variable frequency oscillator that is connected to a signal converter means in a concept that functions to transition a switching means into energizing a modulating propagation means when said sensor upon having manifested a micturition event has prompted said oscillator to react into said signal converter means with a signature frequency characteristic of micturition manifestation; and
   a portable second casing with embodied capture means the output of which into a signal converter means operates in a concept that functions to transition a switching means embodied in said second casing into switching on an alarm configuration that injects its characteristic modulation into the signal circuitry of a baby listening device after said capture means acquisitioned the propagated modulation representative of micturition manifestation.

7. An apparatus for the remote sensing of a micturition manifestation in the space between the outer surface of swaddling and the swaddled, comprising:
- a suitably prepared biological fluid sensor for receiving and transmitting the manifestation of micturition;
- a casing for suitably connecting said sensor and establishing electrical contacts with an embodied acquisitioning means adapted to driving a variable frequency oscillator that is connected to a signal converter means in a concept to transition a switching means into energizing a code modulator means and a thereto connected coded modulation propagation means when said sensor upon having manifested a micturition event has prompted said oscillator to react into said converter with a signature frequency characteristic of micturition manifestation; and
- a portable second casing with embodied capture means the output of which into a signal converter means that is conceptualized upon coded modulation acquisition to result in the origination of a transition in a switching means embodied in said second casing into switching on an alarm configuration that injects its characteristic modulation into the signal circuitry of a baby listening device after said capture means acquisitioned the modulation of propagated code representative of micturition manifestation.

8. An apparatus for the remote sensing of a micturition manifestation in the space between the outer surface of swaddling and the swaddled, comprising:
- a suitably prepared biological fluid sensor for receiving and transmitting the manifestation of micturition;
- a case for suitably connecting to said sensor and establishing electrical contacts with an embodied acquisitioning means adapted to driving a variable frequency oscillator to the signature frequency of a manifestation of micturition; and
- a signal converter means configured for specific frequency recognition that is receivably connected to said signature frequency in a manner that upon variation of frequency by said oscillator to said signature frequency as a result of said sensor receiving the manifestation of micturition there results the origination of a transition by a switching means embodied in the system of a baby listening device causing an alarm configuration to inject its characteristic modulation into the system of a baby listening device and thereby alerting in addition to normal baby's room noises also to the manifestation of micturition when it occurs.

9. An apparatus for the remote listening of a micturition manifestation in the space between the outer surface of swaddling and the swaddled, comprising:
- a detachable casing for suitably interfacing with a correspondingly provided micturitionable means wherein said casing establishes electrical contacts with an embodied acquisition means adapted to driving a variable frequency oscillator to the signature frequency of a manifestation of micturition; and
- a signal converter means configured for specific frequency recognition that is receivably connected to said signature frequency in a manner that upon variation of frequency by said oscillator to said signature frequency as a result of said micturitionable means receiving the manifestation of micturition there results the origination of a transition by a switching means embodied in the system of a baby listening device that causes an alarm configuration to inject its characteristic modulation into the system of baby listening device and thereby alerts in addition to normal baby's room noises also to the manifestation of micturition when it occurs.

10. An apparatus for the remote listening of a micturition manifestation in the space between the outer surface of swaddling and the swaddled, comprising:
- a detachable enclosure suitably configured for modularly interfacing with suitably provided micturitionable means wherein said casing enclosure establishes electrical contacts with an embodied acquisition means adapted to driving a variable frequency oscillator to the signature frequency of a manifestation of micturition; and
- a signal converter means configured for specific frequency recognition that is receivably connected to said signature frequency in a manner that upon variation of frequency by said oscillator to said signature frequency as a result of said micturition receivable means receiving the manifestation of micturition there results the origination of a transition by a switching means embodied in the system of a baby listening device that causes an alarm configuration to inject its characteristic modulation into the system of baby listening device and thereby alerts in addition to normal baby's room noises also to the manifestation of micturition when it occurs.

11. An apparatus for the remote listening of a micturition manifestation in the space between the outer surface of swaddling and the swaddled, comprising:
- a detachable enclosure suitably configured for modularly interfacing with suitably provided micturitionable means wherein said casing enclosure establishes electrical contacts with an embodied acquisition means adapted to driving a variable frequency oscillator to the signature frequency of a manifestation of micturition;
- a modulation accepting propagation means connected into the output of said oscillator; and
- a capture means the output of which into a signal converter means operates in a concept that functions to transition a switching means connected to said signal converter into switching on an alarm configuration that injects its characteristic modulation into the signal circuitry of a baby listening device after said capture means' acquisition and said signal converter's having sampled and found the propagated oscillator's frequency to be representative of manifestation of micturition signature frequency and thereby alerts in addition to normal baby's room noises also to the manifestation of micturition when it occurs.

12. An apparatus for the remote listening of a micturition manifestation in the space between the outer surface of swaddling and the swaddled, comprising:
- a detachable enclosure suitably configured for modularly interfacing with suitably provided micturitionable means wherein said casing enclosure establishes electrical contacts with an embodied acquisition means adapted to driving a variable frequency oscillator that is connected to a signal converter means in a concept that functions to transition a switching means into energizing a modulating propagation means when said micturitionable means upon have manifested a micturition event has prompted said oscillator to react into said signal converter means with a signature frequency characteristic of micturition manifestation; and a capture means the output of which into a signal converter means operates in a concept that functions to transition a switching means connected to said signal converter into switching on an alarm configuration that injects its characteristic modulation into the signal circuitry of a baby listening device after said capture means' acquisition and said signal converter's having sampled and found the propagated oscillator's frequency to be representative of manifestation of micturition signature frequency and thereby alerts in addition to normal baby's room noises also to the manifestation of micturition when it occurs.

13. An apparatus for the remote listening of a micturition manifestation in the space between the outer surface of swaddling and the swaddled, comprising:

a detachable enclosure suitably configured for modularly interfacing with suitably provided micturitionable means wherein said casing enclosure establishes electrical contacts with an embodied acquisitioning means adapted to driving a variable frequency oscillator that is connected to a signal converter means in a concept to transition a switching means into energizing a code modulator means and a thereto connected coded modulation propagation means when said micturitionable means upon having manifested a micturition event has prompted said oscillator to react into said converter with a signature frequency characteristic of micturition manifestation; and a capture means the output of which into a signal converter means is conceptualized upon coded modulation acquisition to result in the origination of a transition in a switching means connected to said signal converter means that switches on an alarm configuration that injects its characteristic modulation into the signal circuitry of a baby listening device after said capture means acquisitioned the modulation of propagated code representative of micturition manifestation and thereby alerts in addition to normal baby's room noises also to the manifestation of micturition when it occurs.

14. An apparatus for the remote listening of a micturition manifestation in the space between the outer surface of swaddling and the swaddled, comprising:

a detachable enclosure suitably configured for modularly interfacing with a suitably provided micturitionable means wherein said casing enclosure establishes electrical contacts with an embodied acquisitioning means adapted to driving a variable frequency oscillator that is connected to a signal converter means in a concept to transition a switching means into energizing a code modulator means and a thereto connected coded modulation propagation means when said micturitionable means upon having manifested a micturition event has prompted said oscillator to react into said converter with a signature frequency characteristic of micturition manifestation; and a portable second casing with embodied capture means the output of which into a signal converter means is conceptualized upon coded modulation acquisition to result in the origination of a transition in a switching means embodied in said second casing into switching on an alarm configuration that injects its characteristic modulation into the signal circuitry of a baby listening device after said capture means acquisitioned the modulation of propagated code representative of micturition manifestation and thereby alerts in addition to normal baby's room noises also to the manifestation of micturition when it occurs.

15. An apparatus for the remote sensing of condensation permeation and a micturition manifestation in the space between the outer surface of swaddling and the swaddled, comprising:

a detachable enclosure suitably configured for modularly interfacing with a suitably provided micturitionable means wherein said enclosure has means to establish electrical impactment contacts with an embodied acquisitioning means adapted to driving a variable frequency oscillator through the signature frequencies of condensation permeation and micturition manifestation; and two signal converter means configured for a lower and a higher frequency recognition that are receivably connected to said signature frequencies in a manner that upon variation of frequency by said oscillator to said lower signature frequency as constitutes the signature frequency of condensation permeation there results the origination of a transition by a switching means out of said lower signature frequency reactive signal converter means that switches on an alarm configuration alerting to the fact of baby's discomfort and susceptibility to suffering from heat rash, and upon variation of frequency to said higher signature frequency constituting evidence of said micturitionable means's manifestation of a micturition there results the origination of a transition by a switching means out of said higher signature frequency reactive signal converter means that switches on a stimulating alarm system, wherein one or more alarms, respectively, are coupled into the propagation circuity of a baby's room listening device thereby to reduce such alert as is configured into said listening device as a signal in addition to normally monitored baby's room noises and, has with it of pocketable type a propagation means, and capture means for employment when baby is removed from the immediate area serviced by said baby's room listening device.

16. An apparatus for the remote sensing of condensation permeation and a micturition manifestation in the space between the outer surface of swaddling and the swaddled, comprising:

a detachable enclosure suitably configured for modularly interfacing with a suitably provided micturitionable means wherein said enclosure has means to establish electrical contacts with an embodied acquisitioning means adapted to driving a variable frequency oscillator through the signature frequencies of condensation permeation and micturition manifestation; and a signal converter means configured for a lower and a higher frequency recognition that is receivably connected to said signature frequencies in a manner that upon variation of frequency by said oscillator to said lower signature frequency as constitutes the signature frequency of condensation permeation there results the origination of a transition by a switching means out of said signal converter means that switches on an alarm configuration alerting to the fact of baby's discomfort and susceptibility to suffering from heat rash, and upon variation of frequency to said higher signature frequency constituting evidence of said micturitionable means' manifestation of a micturition there results the origination of a transition by a switching means out of said signal converter means that switches on a stimulating alarm system, wherein one or more alarms, respectively, are coupled into the propagation circuitry of a baby's room listening device to render such alert as is configured into said device as a signal in addition to normally monitored baby's room noises and, has with it of pocketable type a propagation means, and capture means for employment when baby is removed from the immediate area serviced by said baby's room listening device.

17. An apparatus for alerting to a manifestion of micturition in swaddle and derived equivalent means, comprising:
a detachable enclosure suitably configured to modularly interface with an appropriately provided micturitionable means wherein said enclosure embodies means for an incorporated variable frequency oscillator to interrogate electrical means provided to said micturitionable means and upon a manifestation of micturition, generate a signature frequency signal that is receivable by a signal converter means configured for specific frequency recognition in a manner that upon a variation of frequency by said oscillator to said signature frequency, there results the origination of a transition by a switching means out of said signal converter means that switches an incorporated stimulating alarm system into operation.

18. An apparatus for alerting to a manifestation of micturition in swaddle and derived equivalent means, comprising:
a detachable enclosure suitably configured to modularly interface with an appropriately provided micturitionable means wherein said enclosure embodies means for an incorporated variable frequency oscillator to interrogate electrical means provided to said micturitionable means and upon a manifestation of micturition, generate a signature frequency signal that is receivable by a modulation accepting propagation means connected into the output of said oscillator; and
a pocketable enclosure suitably configured with a capture means the output of which into a signal converter means operates in a concept that functions to transition a switching means connected to said signal converter means into switching an incorporated stimulating alarm system into operation after said capture means' acquisition and said signal converter means having sampled and found said propagated oscillator's frequency to be representative of a manifestation of micturition signature frequency.

19. An apparatus for alerting to a manifestation of micturition in swaddle and derived equivalent means, comprising:
a detachable enclosure suitably configured to modularly interface with an appropriately provided micturitionable means wherein said enclosure embodies means for an incorporated variable frequency oscillator to interrogate electrical means provided to said micturitionable means and upon a manifestation of micturition, generate a signature frequency signal that is connected to a signal converter means in a concept that functions to transition a switching means into energizing a modulation accepting propagation means after said signal converter means had sampled and found said oscillator's frequency to be representative of a manifestation of micturition signature frequency; and
a pocketable enclosure suitably configured with a capture means the output of which into a signal converter means operates in a concept that functions to transition a switching means connected to said signal converter means into switching an incorporated stimulating alarm system into operation after said capture means' acquisition and said signal converter means having sampled and found said propagated oscillator's frequency to be representative of a manifestation of micturition signature frequency.

20. An apparatus for alerting to a manifestation of micturition in swaddle and derived equivalent means, comprising:
a detachable enclosure suitably configured to modularly interface with an appropriately provided micturitionable means wherein said enclosure embodies means for an incorporated variable frequency oscillator to interrogate electrical means provided to said micturitionable means and upon a manifestation of micturition, generate a signature frequency signal that is connected to a signal converter means in a concept that functions to transition a switching means into energizing a self modulated propagation means after said signal converter means had sampled and found said oscillator's frequency to be representative of a manifestation of micturition signature frequency; and
a pocketable enclosure suitably configured with a capture means the output of which into a signal converter means operates in a concept that functions to transition a switching means connected to said signal converter means into switching an incorporating stimulating alarm system into operation after said capture means' acquisition and said signal converter means having sampled and found said self modulated propagated frequency to be representative of an anticipiated frequency representative of a manifestation of micturition.

21. An apparatus for alerting to a manifestation of micturition in swaddle and derived equivalent means, comprising:
a detachable enclosure suitably configured to modularly interface with an appropriately provided micturitionable means wherein said enclosure embodies means for an incorporated variable frequency oscillator to interrogate electrical means provided to said micturitionable means and upon a manifestation of micturition, generate a signature frequency signal that is connected to a signal converter means in a concept that functions to transition a switching means into energizing a modulation accepting propagation means with said signature frequency after said signal converter means had sampled and found said oscillator's frequency to be representative of a manifestation of micturition signature frequency; and
a pocketable enclosure suitably configured with a capture means the output of which created by diode means operates in a concept to energize means that operate an incorporated stimulating alarm system consequential to said capture means' receiving said signature frequency representing a voltage representative of a manifestation of micturition.

22. An apparatus for alerting to a manifestation of micturition in swaddle and derived equivalent means, comprising:

a detachable enclosure suitably configured to modularly interface with an appropriately provided micturitionable means wherein said enclosure embodies means for an incorporated variable frequency oscillator to interrogate electrical means provided to said micturitionable means and upon a manifestation of micturition, generate a signature frequency signal that is connected to a signal converter means in a concept that functions to transition a switching means into energizing a self modulated propagation means after said signal converter means had sampled and found said oscillator's frequency to be representative of a manifestation of micturition signature frequency; and a pocketable enclosure suitably configured with a capture means the output of which created by diode means operates in a concept to energize means that operate an incorporated stimulating alarm system consequential to said capture means' receiving said self modulated propagated frequency representing a voltage representative of a manifestation of micturition.

23. An apparatus for alerting to a manifestation of micturition in swaddle and derived equivalent means, comprising:

a detachable enclosure suitably configured to modularly interface with an appropriately provided micturitionable means wherein said enclosure embodies means for an incorporated variable frequency oscillator to interrogate electrical means provided to said micturitionable means and upon a manifestation of micturition, generate a signature frequency signal that is connected to a signal converter means in a concept that functions to transition a switching means into energizing a code modulator means and a thereto connected coded modulation propagation means when said micturitionable means upon having manifested a micturition event has prompted said oscillator to react with a signature frequency characteristic of micturition manifestation and said switching means out of said signal converter means into energizing said propagation means into propagating coded modulation; and a pocketable enclosure suitably configured with a capture means connected to a compatible signal converter means that is conceptualized upon coded modulation acquisition to result in the origination of a transition by a switching means the operation of which results in directing into operation an incorporated stimulating alarm system.

24. The apparatus as set forth in claim 1, or 2, or 4, or 5, or 6, or 7, or 8, or 9, or 10, or 11, or 12, or 13, or 14, or 15, or 16, or 17, or 18, or 19, or 20, or 21, or 22, or 23, wherein at least one means of a casing enclosure means conceptualized for a capture means, including a detachable enclosure means for clampingly connecting a propagation means to a guest micturitionable means, embodies at least one openable closure means, one of which comprises an electrically functional cavity means characterized with an openable closing means for removably securing a power source means.

25. The apparatus as set forth in claim 1, or 2, or 3, or 4, or 5, or 6, or 7, or 8, or 9, or 10, or 11, or 12, or 13, or 14, or 15, or 16, or 17, or 18, or 19, or 20, or 21, or 22, or 23, wherein at least one means within a detachable enclosure means that is clampingly removable for a guest micturitionable means, including an emplaceable power source means, embodies at least one battery saving configured means arranged in a manner to enable a powered-up condition for a limited duration of time in between a recurring powered-down condition respective to one or more portions of electronic circuitries serviced by said power source means.

26. The apparatus as set forth in claim 2, or 3, or 4, or 5, or 6, or 7, or 8, or 9, or 10, or 11, or 12, or 13, or 14, or 15, or 16, or 18, or 19, or 20, or 21, or 22, or 23, wherein at least one means within the configurability of a capture means' casing enclosure means, including a signal converter means configured for trunking a wireless transmission to a reception capable portion of an electronic circuitry that comprises at least one element of a circuitry means ordinarily consisting of a sending means of a listen-in means, embodies a structural means inherent to a dislodgable child constraining means.

27. The apparatus as set forth in claim 2, or 3, or 4, or 5, or 6, or 7, or 8, or 9, or 10, or 11, or 12, or 14, or 15, or 16, or 18, or 19, or 20, or 21, or 22, or 23, wherein at least one means within a propagation means, including signal converter means, embodies at least one appendage flapper to intercommunicate the representative variations that occur outside of and within said propagation means.

28. The apparatus as set forth in claim 7, or 8, or 9, or 10, or 11, or 12, or 13, or 14, or 15, or 16, or 18, or 19, or 20, or 21, or 22, or 23, wherein at least a portion of a capture means' casing enclosure means, including a signal converter and alarm means, comprises a substantial assimilation of convenience means that include the physical elements, appearance and electrical utility means of a sender's casing means embodying a generic collection of signal collection and processing means comprising a sound transducer means and at least one sound transducer's signal transmitting means characteristical of an electronic babysitter means, thereby in a functional arrangement by impartment, resulting in a sender receiver signal transmittal means that triggers a signal indicating means in a receiver's casing means communicative (1) of a baby's possible sounds and (2) to assert an alert upon a micturitional manifestation by a baby.

29. The apparatus as set forth in claim 7, or 8, or 9, or 10, or 11, or 12, or 13, or 14, or 15, or 16, or 18, or 19, or 20, or 21, or 22, or 23, wherein at least a portion of a capture means, including signal converter means, operates by virtue of an electrical impartment providing an interface with at least one signal path means and at least one power source means that comprises portions of the operational elements of a sender means representative of a sender and receiver means characteristical of an electronic babysitter means, thereby to render said capture means and said operational elements of said sender means to be configured as a utilized means and consequently rendering said capture means operational to modulate said electronic babysitter means when the manifestation of a micturition is monitored by said capture means.

30. A method of producing a biological fluid sensor exhibiting the necessary attributes of softness and hygienic appearance and providing a terraced effect at one edge thereof for communicating with detachable casing enclosures comprising the steps of:
  (a) sectioning from a bulk supply roll of sheet means an appropriate length for clampingly engaging a fusable mat consisting of multiple alternating rows of conducting and insulating means,
  (b) positioning said mat to said sheet in a manner that when said sheet is folded over said mat, said folded portion of sheet is fractionally shorter from fold to edge than the foot-print of sheet to which said mat is positioned, which in its course creates a platform effect of exposed surface of mat and supporting sheet beyond the edge of said folded portion of sheet,
  (c) causing said folds of sheet and said mat to be fused by manufacturing means in a permanently joined configuration, and
  (d) sub-sectioning said joined configuration into multiple straps of micturitionable means by shearing means.

31. A micturitionable means for extending the reach of a detachable apparatus for alerting to a manifestation of micturition that is of semi-disposable variety, exhibits the necessary attributes of softness and hygienic appearance and features its structural arrangement on reversable sides, said micturitionable means comprising:
  a mat consisting of multiple rows of a hot melt conductive means fused in an alternating manner to multiple rows of a hot melt non-conductive means in an arrangement that is permissive of applying shearing guides that may be longitudinally scored along the center of length of each alternate row of non-conductive means so that there may easily be secured a quantity of sectioned straps embodying a centrally located length of non-conductive means shouldered on opposite edges by lengths of conductive means which in turn are shouldered by lengths of a fractionally widthed shoulder of non-conductive means, thereby in configuration providing a micturitionable means that demonstrates equal access to the reciprocal flats of the principal and the reverse sides of derived sections straps.

32. A means as defined in claim 31 for providing enhanced tactile attraction in which said principal and reverse side of said mat is dressed with one side of a unit of sheet that is transversely folded over said mat upon itself along its central axis and secured from removing itself from said mat by securing means employed in the trade.

33. A means as defined in claim 32 for providing a convenient manipulatable platform for injecting directly or via a reuseable interface connector means said mat derived sectioned straps into a mating port of a detachable apparatus for alerting to a manifestation of micturition, in which said unit of sheet is appropriately dimensioned so that when transversely folded over said mat there results full length coverage by said sheet of said reverse side of said mat and fractionally shortened coverage by said sheet of said principal side of said mat, which thereby results in an alternate embodiment whereby is conveniently provided a platform of fractionally exposed mat area along the edge that parallels said fold where originates said fractionally shortened coverage on said principal side of said mat.

34. A means as defined in claim 33, in which said portion of unit of sheet that provides full length coverage of said reverse side of said mat embodies an additional portion of said sheet for providing said sheet a means whereby said additional portion may be folded over the edge of said mat and positioned down over said fractionally exposed mat area and preferably also a portion of said sheet that provides fractionally shortened coverage, thereby serving as a removable contaminated mat deterring flap, the disposal of which prior to operational deployment is facilitated by means of an applied perforated tear line in said location where said additional portion is folded.

35. A means as defined in claim 34, in which said additional portion of said full length coverage portion of unit of sheet is releasably secured in said positioned down configuration by the service of a securing means.

36. A means as defined in claim 34, in which said portion of unit of sheet that provides full length coverage of said reverse side of said mat embodies an additional portion of said sheet for providing said sheet a pull-tab assist feature comprising a folded over provision to said removable contaminated mat deterring flap, wherein an applied perforated tear line in the location where said positioned down portion secures contiguous with said portion of sheet that provides fractionally shortened coverage creates a release assist in the deployment preparation of said means.

37. A means as defined in claim 31 for providing said derived sectioned straps an employment in place and stead of the moisture-permeable porous sheet material that coextensive with a moisture-impermeable backing sheet constitute the key elements of the closed envelope that characterizes the embodiment of disposable diapers as micturitionable means, in which said principal and said reverse side of each derived sectioned strap
  (a) is dressed with one side of a unit of suitably task dimensioned sheet that is transversely folded over said derived sectioned strap upon itself along its central axis,
  (b) said sheet secured from removing itself from said derived sectioned strap by securing means employed in the trade, and
  (c) said sheet provided the dimensional characterization of said diaper sheet material that said folded sheet is conformed to substitute in place and stead.

38. A means as defined in claim 37 for providing a convenient platform to which may conveniently be secured a detachable apparatus for alerting to a manifestation of micturition, in which said unit of sheet is appropriately sized so that when transversely folded over said derived sectioned strap there results full length coverage by said sheet of said reverse side of said derived sectioned strap and fractionally shortened coverage by said sheet of said principal side of said derived sectioned strap, which thereby results in a conveniently provided platform of fractionally exposed derived sectioned strap along the edge that parallels said fold where originates said fractionally shortened coverage on said principal side of said derived sectioned strap.

39. A means as defined in claim 38, in which said means comprises a sheet affixed by securing means to said moisture-impermeable sheet in a manner that arranges for said closed envelope configuration that constitutes the characterization of embodiment presented by disposable diapers as leak-inhibiting micturitionable means.

40. A means as defined in claim 38, in which said portion of unit of sheet that provides full length coverage of said reverse side of said mat and said portion of unit of sheet that provides fractionally shortened coverage of said principal side of said mat comprise discrete units of sheet.

41. A means as defined in claim 37, in which said means comprises a sheet affixed by securing means to said moisture-impermeable sheet in a manner that arranges for said closed envelope configuration that constitutes the characterization of embodiment presented by disposable diapers as leak-inhibiting micturitionable means.

* * * * *